United States Patent [19]

Henderson

[11] Patent Number: 5,648,478

[45] Date of Patent: Jul. 15, 1997

[54] TISSUE-SPECIFIC ENHANCER ACTIVE IN PROSTATE

[76] Inventor: Daniel R. Henderson, 769 Garland Dr., Palo Alto, Calif. 94303

[21] Appl. No.: 380,916

[22] Filed: Jan. 30, 1995

Related U.S. Application Data

[63] Continuation-in-part of Ser. No. 182,247, Jan. 13, 1994.
[51] Int. Cl.$^6$ .......................... C07H 21/04; C12N 15/63
[52] U.S. Cl. ........................... 536/241; 435/320.1
[58] Field of Search ............... 514/44; 536/24.1; 435/320.1

[56] References Cited

FOREIGN PATENT DOCUMENTS

WO94/03594  2/1994  WIPO .

OTHER PUBLICATIONS

Riegman, Genomics, 14: 6–11 (1992).
Haddada, Human Gene Therapy, 4:703–711 (1993).
Nabel, Human Gene Therapy, 3:399–410 (1992).
Trapman, J. Cell Biochem, 48 (16 PAHC), L433 (1992).
Maxwell, Cancer Research, 46: 4660–4664 (1986).
Riegman, Molecular Endocrinology, 5: 1921–1930 (1991).
Brewster, Eur. Urol., 25:177–182 (1994).
Sanda, Urology, 44(4): 617–624 (1994).
Taneja, Surgical Forum, 45: 802–805 (1994).
Luke, Journal of Andrology, 15(1):41–51 (1994).
Taneja, Oncology, 491A, 1056 (1994).
Taneja, Proceedings of the American Association for Cancer Research, 35:375 (1994).
Taneja, Cancer Surveys, 23: 247–266 (1995).
Henttu, et al., cDNA Coding for the Entire Human Prostate Specific Antigen Shows High Homologies to the Human Tissue Kallikrein Genes (Apr. 28, 1989) Biochemical and Biophysical Research Communications, pp. 903–910.
Lundwall, Characterization of the Gene for Prostate–Specific Antigen, A Human Gladnular Kallikrein (Jun. 30, 1989) Biochemical and Biophysical Research Communications, pp. 1151–1159.
Young, et al., Tissue–Specific and Hormonal Regulation of Human Prostate–Specific Glandular Kallikrein (1992) Biochemistry 31:818–824.
Wolf, et al., Transcriptional Regulation of Prostate Kallikrein–Like Genes by Androgen (1992) Molecular Endocrinology, pp. 753–762/.

*Primary Examiner*—Jacqueline M. Stone
*Assistant Examiner*—D. Curtis Hogue, Jr.

[57]   ABSTRACT

The invention provides a human prostate-specific transcriptional regulatory sequence, polynucleotide comprising such regulatory regions, toxin gene constructs wherein a toxin gene is expressed under the transcriptional control of a human prostate-specific transcriptional regulatory sequence, and methods for treating prostate disease using such toxin gene constructs.

5 Claims, 18 Drawing Sheets

Sequence Range: -5824 to 12

>HinDIII

```
         -5820-5815  -5810-5805  -5800-5795  -5790-5785  -5780-5775  -5770-5765
             *           *           *           *           *           *
         AAGCTTCTAG  TTTTCTTTTC  CCGGTGACAT  CGTGGAAAGC  ACTAGCATCT  CTAAGCAATG

-5760-5755  -5750-5745  -5740-5735  -5730-5725  -5720-5715  -5710-5705
             *           *           *           *           *           *
         ATCTGTGACA  ATATTCACAG  TGTAATGCCA  TCCAGGGAAC  TCAACTGAGC  CTTGATGTCC

-5700-5695  -5690-5685  -5680-5675  -5670-5665  -5660-5655  -5650-5645
             *           *           *           *           *           *
         AGAGATTTTT  GTGTTTTTTT  CTGAGACTGA  GTCTCGCTCT  GTGCCAGGCT  GGAGTGCAGT

-5640-5635  -5630-5625  -5620-5615  -5610-5605  -5600-5595  -5590-5585
             *           *           *           *           *           *
         GGTGCAACCT  TGGCTCACTG  CAAGCTCCGC  CTCCTGGGTT  CACGCCATTC  TCCTGCCTCA

-5580-5575  -5570-5565  -5560-5555  -5550-5545  -5540-5535  -5530-5525
             *           *           *           *           *           *
         GCCTCCTGAG  TAGCTGGGAC  TACAGGCACC  CGCCACCACG  CCTGGCTAAT  TTTTTTGTAT

-5520-5515  -5510-5505  -5500-5495  -5490-5485  -5480-5475  -5470-5465
             *           *           *           *           *           *
         TTTTAGTAGA  GATGGGGTTT  CACTGTGTTA  GCCAGGATGG  TCTCAGTCTC  CTGACCTCGT

-5460-5455  -5450-5445  -5440-5435  -5430-5425  -5420-5415  -5410-5405
             *           *           *           *           *           *
         GATCTGCCCA  CCTTGGCCTC  CCAAAGTGCT  GGGATGACAG  GCGTGAGCCA  CCGCGCCTGG

-5400-5395  -5390-5385  -5380-5375  -5370-5365  -5360-5355  -5350-5345
             *           *           *           *           *           *
         CCGATATCCA  GAGATTTTTT  GGGGGGCTCC  ATCACACAGA  CATGTTGACT  GTCTTCATGG

>XbaI
                                   |
         -5340-5335  -5330-5325  -5320-5315  -5310-5305  -5300-5295  -5290-5285
             *           *       |   *           *           *           *
         TTGACTTTTA  GTATCCAGCC  CCTCTAGAAA  TCTAGCTGAT  ATAGTGTGGC  TCAAAACCTT

-5280-5275  -5270-5265  -5260-5255  -5250-5245  -5240-5235  -5230-5225
             *           *           *           *           *           *
         CAGCACAAAT  CACACCGTTA  GACTATCTGG  TGTGGCCCAA  ACCTTCAGGT  GAACAAAGGG

-5220-5215  -5210-5205  -5200-5195  -5190-5185  -5180-5175  -5170-5165
             *           *           *           *           *           *
         ACTCTAATCT  GGCAGGATAT  TCCAAAGCAT  TAGAGATGAC  CTCTTGCAAA  GAAAAGAAA

-5160-5155  -5150-5145  -5140-5135  -5130-5125  -5120-5115  -5110-5105
             *           *           *           *           *           *
         TGGAAAAGAA  AAAGAAAGAA  AGGAAAAAAA  AAAAAAAAAA  GAGATGACCT  CTCAGGCTCT

-5100-5095  -5090-5085  -5080-5075  -5070-5065  -5060-5055  -5050-5045
             *           *           *           *           *           *
         GAGGGGAAAC  GCCTGAGGTC  TTTGAGCAAG  GTCAGTCCTC  TGTTGCACAG  TCTCCCTCAC
```

FIG. 1A

```
-5040-5035  -5030-5025  -5020-5015  -5010-5005  -5000-4995  -4990-4985
     *           *           *           *           *           *
AGGGTCATTG  TGACGATCAA  ATGTGGTCAC  GTGTATGAGG  CACCAGCACA  TGCCTGGCTC

-4980-4975  -4970-4965  -4960-4955  -4950-4945  -4940-4935  -4930-4925
     *           *           *           *           *           *
TGGGGAGTGC  CGTGTAAGTG  TATGCTTGCA  CTGCTGAATG  CTTGGGATGT  GTCAGGGATT

-4920-4915  -4910-4905  -4900-4895  -4890-4885  -4880-4875  -4870-4865
     *           *           *           *           *           *
ATCTTCAGCA  CTTACAGATG  CTCATCTCAT  CCTCACAGCA  TCACTATGGG  ATGGGTATTA

-4860-4855  -4850-4845  -4840-4835  -4830-4825  -4820-4815  -4810-4805
     *           *           *           *           *           *
CTGGCCTCAT  TTGATGGAGA  AAGTGGCTGT  GGCTCAGAAA  GGGGGGACCA  CTAGACCAGG

>PstI
                                                    |
-4800-4795  -4790-4785  -4780-4775  -4770-4765  -4760-4755  -4750-4745
     *           *           *           *        |  *           *
GACACTCTGG  ATGCTGGGA   CTCCAGAGAC  CATGACCACT  CACCAACTGC  AGAGAAATTA

-4740-4735  -4730-4725  -4720-4715  -4710-4705  -4700-4695  -4690-4685
     *           *           *           *           *           *
ATTGTGGCCT  GATGTCCCTG  TCCTGGAGAG  GGTGGAGGTG  GACCTTCACT  AACCTCCTAC

-4680-4675  -4670-4665  -4660-4655  -4650-4645  -4640-4635  -4630-4625
     *           *           *           *           *           *
CTTGACCCTC  TCTTTTAGGG  CTCTTTCTGA  CCTCCACCAT  GGTACTAGGA  CCCCATTGTA

-4620-4615  -4610-4605  -4600-4595  -4590-4585  -4580-4575  -4570-4565
     *           *           *           *           *           *
TTCTGTACCC  TCTTGACTCT  ATGACCCCCA  CTGCCCACTG  CATCCAGCTG  GGTCCCCTCC

-4560-4555  -4550-4545  -4540-4535  -4530-4525  -4520-4515  -4510-4505
     *           *           *           *           *           *
TATCTCTATT  CCCAGCTGGC  CAGTGCAGTC  TCAGTGCCCA  CCTGTTTGTC  AGTAACTCTG

-4500-4495  -4490-4485  -4480-4475  -4470-4465  -4460-4455  -4450-4445
     *           *           *           *           *           *
AAGGGGCTGA  CATTTTACTG  ACTTGCAAAC  AAATAAGCTA  ACTTTCCAGA  GTTTTGTGAA

-4440-4435  -4430-4425  -4420-4415  -4410-4405  -4400-4395  -4390-4385
     *           *           *           *           *           *
TGCTGGCAGA  GTCCATGAGA  CTCCTGAGTC  AGAGGCAAAG  GCTTTTACTG  CTCACAGCTT

-4380-4375  -4370-4365  -4360-4355  -4350-4345  -4340-4335  -4330-4325
     *           *           *           *           *           *
AGCAGACAGC  ATGAGGTTCA  TGTTCACATT  AGTACACCTT  GCCCCCCCCA  AATCTTGTAG

-4320-4315  -4310-4305  -4300-4295  -4290-4285  -4280-4275  -4270-4265
     *           *           *           *           *           *
GGTGACCAGA  GCAGTCTAGG  TGGATGCTGT  GCAGAAGGGG  TTTGTGCCAC  TGGTGAGAAA

-4260-4255  -4250-4245  -4240-4235  -4230-4225  -4220-4215  -4210-4205
     *           *           *           *           *           *
CCTGAGATTA  GGAATCCTCA  ATCTTATACT  GGGACAACTT  GCAAACCTGC  TCAGCCTTTG
```

FIG. 1B

```
-4200-4195  -4190-4185  -4180-4175  -4170-4165  -4160-4155  -4150-4145
     *           *           *           *           *           *
TCTCTGATGA  AGATATTATC  TTCATGATCT  TGGATTGAAA  ACAGACCTAC  TCTGGAGGAA

>ClaI
         |
-4140-4135  -4130-4125  -4120-4115  -4110-4105  -4100-4095  -4090-4085
    |*           *           *           *           *           *
CATATTGTAT  CGATTGTCCT  TGACAGTAAA  CAAATCTGTT  GTAAGAGACA  TTATCTTTAT

-4080-4075  -4070-4065  -4060-4055  -4050-4045  -4040-4035  -4030-4025
     *           *           *           *           *           *
TATCTAGGAC  AGTAAGCAAG  CCTGGATCTG  AGAGAGATAT  CATCTTGCAA  GGATGCCTGC

-4020-4015  -4010-4005  -4000-3995  -3990-3985  -3980-3975  -3970-3965
     *           *           *           *           *           *
TTTACAAACA  TCCTTGAAAC  AACAATCCAG  AAAAAAAAAG  GTGTTGCTGT  CTTTGCTCAG

-3960-3955  -3950-3945  -3940-3935  -3930-3925  -3920-3915  -3910-3905
     *           *           *           *           *           *
AAGACACACA  GATACGTGAC  AGAACCATGG  AGAATTGCCT  CCCAACGCTG  TTCAGCCAGA

>PstI
               |
-3900-3895  -3890-3885  -3880-3875  -3870-3865  -3860-3855  -3850-3845
     *          |*           *           *           *           *
GCCTTCCACC  CTTGTCTGCA  GGACAGTCTC  AACGTTCCAC  CATTAAATAC  TTCTTCTATC

-3840-3835  -3830-3825  -3820-3815  -3810-3805  -3800-3795  -3790-3785
     *           *           *           *           *           *
ACATCCTGCT  TCTTTATGCC  TAACCAAGGT  TCTAGGTCCC  GATCGACTGT  GTCTGGCAGC

>BamHI
                                       |
-3780-3775  -3770-3765  -3760-3755  -3750-3745  -3740-3735  -3730-3725
     *           *           *          |*           *           *
ACTCCACTGC  CAAACCCAGA  ATAAGGCAGC  GCTCAGGATC  CCGAAGGGGC  ATGGCTGGGG

-3720-3715  -3710-3705  -3700-3695  -3690-3685  -3680-3675  -3670-3665
     *           *           *           *           *           *
ATCAGAACTT  CTGGGTTTGA  GTGAGGAGTG  GGTCCACCCT  CTTGAATTTC  AAAGGAGGAA

-3660-3655  -3650-3645  -3640-3635  -3630-3625  -3620-3615  -3610-3605
     *           *           *           *           *           *
GAGGCTGGAT  GTGAAGGTAC  TGGGGGAGGG  AAAGTGTCAG  TTCCGAACTC  TTAGGTCAAT

-3600-3595  -3590-3585  -3580-3575  -3570-3565  -3560-3555  -3550-3545
     *           *           *           *           *           *
GAGGGAGGAG  ACTGGTAAGG  TCCCAGCTCC  CGAGGTACTG  ATGTGGGAAT  GGCCTAAGAA

-3540-3535  -3530-3525  -3520-3515  -3510-3505  -3500-3495  -3490-3485
     *           *           *           *           *           *
TCTCATATCC  TCAGGAAGAA  GGTGCTGGAA  TCCTGAGGGG  TAGAGTTCTG  GGTATATTTG

-3480-3475  -3470-3465  -3460-3455  -3450-3445  -3440-3435  -3430-3425
     *           *           *           *           *           *
TGGCTTAAGG  CTCTTTGGCC  CCTGAAGGCA  GAGGCTGGAA  CCATTAGGTC  CAGGGTTTGG
```

FIG. 1C

```
-3420-3415  -3410-3405  -3400-3395  -3390-3385  -3380-3375  -3370-3365
    *           *           *           *           *           *
GGTGATAGTA  ATGGGATCTC  TTGATTCCTC  AAGAGTCTGA  GGATCGAGGG  TTGCCCATTC

-3360-3355  -3350-3345  -3340-3335  -3330-3325  -3320-3315  -3310-3305
    *           *           *           *           *           *
TTCCATCTTG  CCACCTAATC  CTTACTCCAC  TTGAGGGTAT  CACCAGCCCT  TCTAGCTCCA

-3300-3295  -3290-3285  -3280-3275  -3270-3265  -3260-3255  -3250-3245
    *           *           *           *           *           *
TGAAGGTCCC  CTGGGCAAGC  ACAATCTGAG  CATGAAAGAT  GCCCCAGAGG  CCTTGGGTGT

-3240-3235  -3230-3225  -3220-3215  -3210-3205  -3200-3195  -3190-3185
    *           *           *           *           *           *
CATCCACTCA  TCATCCAGCA  TCACACTCTG  AGGGTGTGGC  CAGCACCATG  ACGTCATGTT

>PstI
               |
-3180-3175  -3170-3165  -3160-3155  -3150-3145  -3140-3135  -3130-3125
    *          |*           *           *           *           *
GCTGTGACTA  TCCCTGCAGC  GTGCCTCTCC  AGCCACCTGC  CAACCGTAGA  GCTGCCCATC

-3120-3115  -3110-3105  -3100-3095  -3090-3085  -3080-3075  -3070-3065
    *           *           *           *           *           *
CTCCTCTGGT  GGGAGTGGCC  TGCATGGTGC  CAGGCTGAGG  CCTAGTGTCA  GACAGGGAGC

>BamHI
               |
-3060-3055  -3050-3045  -3040-3035  -3030-3025  -3020-3015  -3010-3005
    *          |*           *           *           *           *
CTGGAATCAT  AGGGATCCAG  GACTCAAAAG  TGCTAGAGAA  TGGCCATATG  TCACCATCCA

-3000-2995  -2990-2985  -2980-2975  -2970-2965  -2960-2955  -2950-2945
    *           *           *           *           *           *
TGAAATCTCA  AGGGCTTCTG  GGTGGAGGGC  ACAGGGACCT  GAACTTATGG  TTTCCCAAGT

-2940-2935  -2930-2925  -2920-2915  -2910-2905  -2900-2895  -2890-2885
    *           *           *           *           *           *
CTATTGCTCT  CCCAAGTGAG  TCTCCCAGAT  ACGAGGCACT  GTGCCAGCAT  CAGCCTTATC

>ApaI
                           |
-2880-2875  -2870-2865  -2860-2855  -2850-2845  -2840-2835  -2830-2825
    *           *           *           *           *           *
TCCACCACAT  CTTGTAAAAG  GACTACCCAG  GGCCCTGATG  AACACCATGG  TGTGTACAGG

-2820-2815  -2810-2805  -2800-2795  -2790-2785  -2780-2775  -2770-2765
    *           *           *           *           *           *
AGTAGGGGGT  GGAGGCACGG  ACTCCTGTGA  GGTCACAGCC  AAGGGAGCAT  CATCATGGGT

-2760-2755  -2750-2745  -2740-2735  -2730-2725  -2720-2715  -2710-2705
    *           *           *           *           *           *
GGGGAGGAGG  CAATGGACAG  GCTTGAGAAC  GGGGATGTGG  TTGTATTTGG  TTTTCTTTGG

-2700-2695  -2690-2685  -2680-2675  -2670-2665  -2660-2655  -2650-2645
    *           *           *           *           *           *
TTAGATAAAG  TGCTGGGTAT  AGGATTGAGA  GTGGAGTATG  AAGACCAGTT  AGGATGGAGG
```

FIG. 1D

```
-2640-2635  -2630-2625  -2620-2615  -2610-2605  -2600-2595  -2590-2585
     *           *           *           *           *           *
ATCAGATTGG  AGTTGGGTTA  GATAAAGTGC  TGGGTATAGG  ATTGAGAGTG  GAGTATGAAG

-2580-2575  -2570-2565  -2560-2555  -2550-2545  -2540-2535  -2530-2525
     *           *           *           *           *           *
ACCAGTTAGG  ATGGAGGATC  AGATTGGAGT  TGGGTTAGAG  ATGGGGTAAA  ATTGTGCTCC

-2520-2515  -2510-2505  -2500-2495  -2490-2485  -2480-2475  -2470-2465
     *           *           *           *           *           *
GGATGAGTTT  GGGATTGACA  CTGTGGAGGT  GGTTTGGGAT  GGCATGGCTT  TGGGATGGAA

-2460-2455  -2450-2445  -2440-2435  -2430-2425  -2420-2415  -2410-2405
     *           *           *           *           *           *
ATAGATTTGT  TTTGATGTTG  GCTCAGACAT  CCTTGGGGAT  TGAACTGGGG  ATGAAGCTGG

-2400-2395  -2390-2385  -2380-2375  -2370-2365  -2360-2355  -2350-2345
     *           *           *           *           *           *
GTTTGATTTT  GGAGGTAGAA  GACGTGGAAG  TAGCTGTCAG  ATTTGACAGT  GGCCATGAGT

-2340-2335  -2330-2325  -2320-2315  -2310-2305  -2300-2295  -2290-2285
     *           *           *           *           *           *
TTTGTTTGAT  GGGGAATCAA  ACAATGGGGG  AAGACATAAG  GGTTGGCTTG  TTAGGTTAAG

-2280-2275  -2270-2265  -2260-2255  -2250-2245  -2240-2235  -2230-2225
     *           *           *           *           *           *
TTGCGTTGGG  TTGATGGGGT  CGGGGCTGTG  TATAATGCAG  TTGGATTGGT  TTGTATTAAA

>BamHI
                                                              |
-2220-2215  -2210-2205  -2200-2195  -2190-2185  -2180-2175  -2170-2165
     *           *           *           *           *      |    *
TTGGGTTGGG  TCAGGTTTTG  GTTGAGGATG  AGTTGAGGAT  ATGCTTGGGG  ACACCGGATC

-2160-2155  -2150-2145  -2140-2135  -2130-2125  -2120-2115  -2110-2105
     *           *           *           *           *           *
CATGAGGTTC  TCACTGGAGT  GGAGACAAAC  TTCCTTTCCA  GGATGAATCC  AGGGAAGCCT

-2100-2095  -2090-2085  -2080-2075  -2070-2065  -2060-2055  -2050-2045
     *           *           *           *           *           *
TAATTCACGT  GTAGGGGAGG  TCAGGCCACT  GGCTAAGTAT  ATCCTTCCAC  TCCAGCTCTA

-2040-2035  -2030-2025  -2020-2015  -2010-2005  -2000-1995  -1990-1985
     *           *           *           *           *           *
AGATGGTCTT  AAATTGTGAT  TATCTATATC  CACTTCTGTC  TCCCTCACTG  TGCTTGGAGT

-1980-1975  -1970-1965  -1960-1955  -1950-1945  -1940-1935  -1930-1925
     *           *           *           *           *           *
TTACCTGATC  ACTCAACTAG  AAACAGGGGA  AGATTTATC   AAATTCTTTT  TTTTTTTTTT

-1920-1915  -1910-1905  -1900-1895  -1890-1885  -1880-1875  -1870-1865
     *           *           *           *           *           *
TTTTTTTTGA  GACAGAGTCT  CACTCTGTTG  CCCAGGCTGG  AGTGCAGTGG  CGCAGTCTCG

-1860-1855  -1850-1845  -1840-1835  -1830-1825  -1820-1815  -1810-1805
     *           *           *           *           *           *
GCTCACTGCA  ACCTCTGCCT  CCCAGGTTCA  AGTGATTCTC  CTGCCTCAGC  CTCCTGAGTT
```

FIG. 1E

```
-1800-1795  -1790-1785  -1780-1775  -1770-1765  -1760-1755  -1750-1745
     *           *           *           *           *           *
GCTGGGATTA  CAGGCATGCA  GCACCATGCC  CAGCTAATTT  TTGTATTTTT  AGTAGAGATG

-1740-1735  -1730-1725  -1720-1715  -1710-1705  -1700-1695  -1690-1685
     *           *           *           *           *           *
GGGTTTCACC  AATGTTTGCC  AGGCTGGCCT  CGAACTCCTG  ACCTGGTGAT  CCACCTGCCT

-1680-1675  -1670-1665  -1660-1655  -1650-1645  -1640-1635  -1630-1625
     *           *           *           *           *           *
CAGCCTCCCA  AAGTGCTGGG  ATTACAGGCG  TCAGCCACCG  CGCCCAGCCA  CTTTTGTCAA

-1620-1615  -1610-1605  -1600-1595  -1590-1585  -1580-1575  -1570-1565
     *           *           *           *           *           *
ATTCTTGAGA  CACAGCTCGG  GCTGGATCAA  GTGAGCTACT  CTGGTTTTAT  TGAACAGCTG

>KpnI
                                                          |
-1560-1555  -1550-1545  -1540-1535  -1530-1525  -1520-1515  -1510-1505
     *           *           *           *           *       |   *
AAATAACCAA  CTTTTTGGAA  ATTGATGAAA  TCTTACGGAG  TTAACAGTGG  AGGTACCAGG

-1500-1495  -1490-1485  -1480-1475  -1470-1465  -1460-1455  -1450-1445
     *           *           *           *           *           *
GCTCTTAAGA  GTTCCCGATT  CTCTTCTGAG  ACTACAAATT  GTGATTTGC   ATGCCACCTT

-1440-1435  -1430-1425  -1420-1415  -1410-1405  -1400-1395  -1390-1385
     *           *           *           *           *           *
AATCTTTTTT  TTTTTTTTTT  TAAATCGAGG  TTTCAGTCTC  ATTCTATTTC  CCAGGCTGGA

-1380-1375  -1370-1365  -1360-1355  -1350-1345  -1340-1335  -1330-1325
     *           *           *           *           *           *
GTTCAATAGC  GTGATCACAG  CTCACTGTAG  CCTTGAACTC  CTGGCCTTAA  GAGATTCTCC

-1320-1315  -1310-1305  -1300-1295  -1290-1285  -1280-1275  -1270-1265
     *           *           *           *           *           *
TGCTTCGGTC  TCCCAATAGC  TAAGACTACA  GTAGTCCACC  ACCATATCCA  GATAATTTTT

-1260-1255  -1250-1245  -1240-1235  -1230-1225  -1220-1215  -1210-1205
     *           *           *           *           *           *
AAATTTTTTG  GGGGGCCGGG  CACAGTGGCT  CACGCCTGTA  ATCCCAACAC  CATGGGAGGC

-1200-1195  -1190-1185  -1180-1175  -1170-1165  -1160-1155  -1150-1145
     *           *           *           *           *           *
TGAGATGGGT  GGATCACGAG  GTCAGGAGTT  TGAGACCAGC  CTGACCAACA  TGGTGAAACT

-1140-1135  -1130-1125  -1120-1115  -1110-1105  -1100-1095  -1090-1085
     *           *           *           *           *           *
CTGTCTCTAC  TAAAAAAAAA  AAAAATAGAA  AAATTAGCCG  GGCGTGGTGG  CACACGGCAC

-1080-1075  -1070-1065  -1060-1055  -1050-1045  -1040-1035  -1030-1025
     *           *           *           *           *           *
CTGTAATCCC  AGCTACTGAG  GAGGCTGAGG  CAGGAGAATC  ACTTGAACCC  AGAAGGCAGA

-1020-1015  -1010-1005   -1000 -995   -990 -985   -980 -975   -970 -965
     *           *           *           *           *           *
GGTTGCAATG  AGCCGAGATT  GCGCCACTGC  ACTCCAGCCT  GGGTGACAGA  GTGAGACTCT
```

FIG. 1F

```
    -960 -955    -950 -945    -940 -935    -930 -925    -920 -915    -910 -905
         *            *            *            *            *            *
    GTCTCAAAAA   AAAAAAATTT   TTTTTTTTTT   TTTGTAGAGA   TGGATCTTGC   TTTGTTTCTC

-900 -895    -890 -885    -880 -875    -870 -865    -860 -855    -850 -845
         *            *            *            *            *            *
    TGGTTGGCCT   TGAACTCCTG   GCTTCAAGTG   ATCCTCCTAC   CTTGGCCTCG   GAAAGTGTTG

-840 -835    -830 -825    -820 -815    -810 -805    -800 -795    -790 -785
         *            *            *            *            *            *
    GGATTACAGG   CGTGAGCCAC   CATGACTGAC   CTGTCGTTAA   TCTTGAGGTA   CATAAACCTG

-780 -775    -770 -765    -760 -755    -750 -745    -740 -735    -730 -725
         *            *            *            *            *            *
    GCTCCTAAAG   GCTAAAGGCT   AAATATTTGT   TGGAGAAGGG   GCATTGGATT   TTGCATGAGG

-720 -715    -710 -705    -700 -695    -690 -685    -680 -675    -670 -665
         *            *            *            *            *            *
    ATGATTCTGA   CCTGGGAGGG   CAGGTCAGCA   GGCATCTCTG   TTGCACAGAT   AGAGTGTACA

>EcoRI
                                          |
    -660 -655    -650 -645    -640 -635   -630 -625    -620 -615    -610 -605
         *            *            *    |      *            *            *
    GGTCTGGAGA   ACAAGGAGTG   GGGGGTTATT   GGAATTCCAC   ATTGTTTGCT   GCACGTTGGA

-600 -595    -590 -585    -580 -575    -570 -565    -560 -555    -550 -545
         *            *            *            *            *            *
    TTTTGAAATG   CTAGGGAACT   TTGGGAGACT   CATATTTCTG   GGCTAGAGGA   TCTGTGGACC

-540 -535    -530 -525    -520 -515    -510 -505    -500 -495    -490 -485
         *            *            *            *            *            *
    ACAAGATCTT   TTTATGATGA   CAGTAGCAAT   GTATCTGTGG   AGCTGGATTC   TGGGTTGGGA

-480 -475    -470 -465    -460 -455    -450 -445    -440 -435    -430 -425
         *            *            *            *            *            *
    GTGCAAGGAA   AAGAATGTAC   TAAATGCCAA   GACATCTATT   TCAGGAGCAT   GAGGAATAAA

-420 -415    -410 -405    -400 -395    -390 -385    -380 -375    -370 -365
         *            *            *            *            *            *
    AGTTCTAGTT   TCTGGTCTCA   GAGTGGTGCA   GGGATCAGGG   AGTCTCACAA   TCTCCTGAGT

-360 -355    -350 -345    -340 -335    -330 -325    -320 -315    -310 -305
         *            *            *            *            *            *
    GCTGGTGTCT   TAGGGCACAC   TGGGTCTTGG   AGTGCAAAGG   ATCTAGGCAC   GTGAGGCTTT

-300 -295    -290 -285    -280 -275    -270 -265    -260 -255    -250 -245
         *            *            *            *            *            *
    GTATGAAGAA   TCGGGGATCG   TACCCACCCC   CTGTTTCTGT   TTCATCCTGG   GCATGTCTCC

-240 -235    -230 -225    -220 -215    -210 -205    -200 -195    -190 -185
         *            *            *            *            *            *
    TCTGCCTTTG   TCCCCTAGAT   GAAGTCTCCA   TGAGCTACAA   GGGCCTGGTG   CATCCAGGGT

-180 -175    -170 -165    -160 -155    -150 -145    -140 -135    -130 -125
         *            *            *            *            *            *
    GATCTAGTAA   TTGCAGAACA   GCAAGTGCTA   GCTCTCCCTC   CCCTTCCACA   GCTCTGGGTG
```

FIG. 1G

```
-120  -115    -110 -105    -100  -95    -90   -85    -80   -75    -70   -65
  *             *            *            *            *            *
TGGGAGGGGG  TTGTCCAGCC  TCCAGCAGCA  TGGGGAGGGC  CTTGGTCAGC  CTCTGGGTGC

-60   -55    -50   -45    -40   -35    -30   -25    -20   -15    -10    -5
  *             *            *            *            *            *
CAGCAGGGCA  GGGGCGGAGT  CCTGGGGAAT  GAAGGTTTTA  TAGGGCTCCT  GGGGGAGGCT

>HinDIII
                  |
  1      6   |  11
  *          |
CCCCAGCCCC  AAGCTT
```

FIG. 1H

```
Sequence Range: -5824 to 12

Enzyme      #Cuts   Positions

Apa1         1      -2851
BamH1        3      -3749      -3052      -2169
Bgl2         1       -541
Cla1         1      -4135
EcoR1        1       -633
Hind3        2      -5824         7
Kpn1         1      -1509
Nde1         1      -3019
Pst1         3      -4754      -3885      -3167
Stu1         2      -3255      -3085
Xba1         1      -5322
```

TISSUE-SPECIFIC ENHANCER ACTIVE IN PROSTATE

CROSS REFERENCE TO RELATED APPLICATIONS

This application is a continuation-in-part of application Ser. No. 08/182,247, filed Jan. 13, 1994.

FIELD OF THE INVENTION

The invention provides novel transcriptional regulatory elements (enhancers) which preferentially enhance the net transcription of cis-linked transcription units in prostate tissue. The tissue-specific prostate enhancers of the present invention are preferentially active in prostatic cells as compared with other tissues- The invention also provides compositions suitable for genetic therapy of prostate hyperplasia and neoplasia, and methods for treating such disease conditions using the navel compositions, which comprise polynucleotides suitable for use as transgenes and/or gene-targeting constructs.

BACKGROUND

BPH. Prostate Neoplasia and Treatment Modalities

There are three significant diseases of the prostate: benign prostate hyperplasia (BPH), prostate cancer, and prostatitis. The costs of these three diseases are immense. In 1985, the annual treatment of prostate diseases in the US required 4.4 million physician visits, 836,000 hospitalizations, and cost over $3 billion. In 1985, the costs for BPH, prostate cancer, and prostatitis were $1.82, $0.97, and $0.29 billion respectively. Clearly these diseases represent a significant percentage of the American health care dollar. In addition prostate cancer caused 39,215 deaths. BPH and prostate cancer are diseases of men over 50. Due to the aging US population, the incidence of BPH and prostate cancer will increase 50% in the next 15 years.

BPH causes urinary obstruction resulting in urinary incontinence. It occurs in almost 80% of men by the age of 80. Unregulated dihydrotestosterone is believed to cause hyperplastic prostate growth in aging men. Pharmcotherapy for the treatment or BPH is currently aimed to relax prostate smooth muscle (alpha blockade) and decrease prostate volume (androgen suppression). Phase III clinical trials are underway evaluating selective $alpha_1$ blockers, anti-androgens, and 5-alpha reductase inhibitors for the treatment of BPH. The most promising of these is finasteride. It has shown an ability to cause regression of the hyperplastic prostate gland in a majority of patients (Mocellini et.al. (1993) Prostate 22:291).

BPH is treated surgically with a transurethral resection of the prostate (TURP). This procedure is most common: 500,000 TURPs are performed in the US each year and 25% of men will require surgery at some time in their lives to alleviate urinary obstruction. This makes BPH the second most common cause of surgery in males after cataract surgery. The TURP procedure requires several days hospitalization as well as the surgery itself. The average medical reimbursement cost of a TURP in 1987 dollars was $8,000; in 1993 dollars this is $14,000. Unfortunately, a side-effect of the TURP is the elimination of the ejaculatory ducts resulting in impotence in 90% of patients. A TURP is prefaced by an outpatient biopsy procedure to determine if the enlargement of the prostate is benign or cancerous.

Prostate cancer is the second most common cause of cancer death in American males where only lung cancer is greater. Prostate cancer is a latent disease; many men carry prostate cancer cells without overt signs of disease. Autopsies of individuals dying of other causes show prostate cancer cells in 30% of men at age 50; by the age of 80 years, the prevalence is 60% of prostates. Further, prostate cancer can take up to 10 years to kill the patient after initial diagnosis. Prostate cancer is newly diagnosed in slightly over 100,000 men in the US. each year of which over 40,000 will die of the disease. There is also high morbidity. Cancer metastasis to bone (late stage) is common and often associated with uncontrollable pain. Metastasis also occurs to lymph nodes (early stage).

The progression of the disease is from a well-defined mass within the prostate, to a breakdown and invasion of the lateral margins of the prostate, to metastasis to regional lymph nodes, to metastasis to the bone marrow. The aggressiveness of prostate tumors varies widely. Some tumors are relatively aggressive, doubling every six months, whereas other are extremely slow-growing, doubling once every five years. As a consequence of the slow growth rate, few cancer cells are actively dividing at any one time. As a result, prostate cancer is generally resistant to radiation and chemotherapy, although both therapeutic modalities are widely used. Surgery is the mainstay of treatment but it too is largely ineffective and also removes the ejaculatory ducts, resulting in impotence.

Unfortunately, in 80% of cases, diagnosis of prostate cancer is established when the disease has already metastasized to the bones. Of special interest is the observation that prostate cancers frequently grow more rapidly in sites of metastasis than within the prostate itself, the site of the primary cancer.

The diagnosis and management of prostate cancer has become simplified with the use of measurement of serum levels of prostate-specific antigen. Prostate-specific antigen (PSA) is a protease involved in the breakdown of the ejaculate coagulum. Serum levels of PSA vary from 2–4 ng/ml and usually a single determination of an individual's PSA level is meaningless. Most frequently PSA levels are elevated in both prostate cancer and BPH. A serum PSA level of over 4 ng/ml usually warrants further investigation. Even more telling are rapid increases in serum PSA levels which can indicate active prostate cancer. A rapid rise in PSA levels from 2–4 ng/ml to over 10 ng/ml indicates active disease (Hamdy, F. C., et al. (1992) Br. J. Urol. 69:392). In end-stage metastatic disease, PSA levels can reach 200 ng/ml. PSA is a single amino acid chain of 240 AA and has been cloned (Lundwall A. and Lilja H. (1987) FEBS Lett 214:317: Lundwall A (1989) Biochem. Biophys. Res. Comm. 161:1151; Riegman et al. (1989) Biochem. Biophys. Res. Comm. 159:95).

For the treatment of prostate cancer oral estrogens and luteinizing releasing hormone analogs are used as well as surgical removal of glands that produce androgens (orchiectomy or adrenalectomy). The Nobel prize was awarded in 1966 to Charles Kuggins for utilizing castration for treatment of prostate cancer. Many patients showed marked improvement after castration, but this was only temporary relief. Most of these cancers soon relapsed and presented as a therapeutically resistant form that ultimately caused death. Current therapeutic techniques use chemical forms of medical castration by shutting down androgen production in the testes, or directly block androgen production in the prostate.

Estrogens are no longer recommended for therapy because of serious, even lethal, cardiovascular complications. Luteinizing hormone releasing hormone (LHRH) analogs are used instead. LHRH analogs are equally effective when compared to estrogens, or orchiectomy. LHRH treatments are reversible, do not involve surgery, and do not impact the patient psychologically. Thus, this treatment is preferable for producing androgenic deprivation. LHRH analogs initially increase pituitary LH secretion with a subsequent increase in serum testosterone. This results in a disease "flare" that rapidly subsides as the initial increase in LHRH-mediated LH secretion is reversed when over stimulation of pituitary LHRH receptors leads to a shutdown in their function and a consequent fall in LH secretion, and thus, testicular testosterone production (Redding et al. (1982) Proc. Natl. Acad. Sci. 79:1273). However, hormonal therapy invariably fails with time with the development of hormone-resistant tumor cells. It is not known whether these cells develop as a mutation of the original hormone sensitive cells, or as a separate class of cells. However, since 20% of patients fail to respond to hormonal therapy, it is believed that hormone-resistant cells are present at the onset of therapy.

Estramustine, a steroidal nitrogen mustard derivative, is undergoing clinical trials for advanced stage prostate cancer. Estramustine was originally thought to be suitable for targeted drug delivery through conjugation of estrogen to toxic nitrogen mustard. Surprisingly however, estramustine has no alkylating or hormonal effects. Rather, estramustine disassembles microtubles inhibiting cell division. Phase II and Phase III clinical trials over the past 15 years have been disappointing when survival is used as an endpoint.

Finasteride, a 4-aza steroid (Proscar® from Merck & Co.) inhibits 5α-reductase, the enzyme responsible for the intracellular conversion of testosterone to dihydrotestosterone in the stroma of the prostate. Since dihydrotestosterone is the most potent androgen in the prostate, its elimination causes regression of prostate cancer by as much as 40% in volume. Casodexthin® is thought to inhibit cellular uptake of testosterone by blocking androgen receptors in the nucleus. However, almost all advanced cancer prostate cells fail to respond to androgen deprivation. At this stage there is no effective cytotoxic chemotherapy for prostate cancer.

A major, indeed the overwhelming, obstacle to cancer therapy is the problem of selectivity; that is, the ability to inhibit the multiplication of tumor cells, while leaving unaffected the function of normal cells. Thus, the therapeutic ratio, or ratio of tumor cell killing to normal cell killing of traditional tumor chemotherapy, is only 1.5:1. Thus, more effective treatment methods and pharmaceutical compositions for therapy and prophylaxis of prostatic hyperplasia and neoplasia are needed.

Transcriptional Regulatory Elements

Methods and compositions are provided for prostate cell specific transcription, particularly human prostate cells comprising prostate specific antigen, a glandular kallikrein. An approximately 2.5 kbp fragment from about −2850 to about −5350 serves as a prostate specific enhancer ("PSE") in conjunction with a promoter to function to initiate transcription in prostate cells. Constructions are provided for identifying cells which have the transcriptional components for regulating transcription in conjunction with the PSE and for genetically modifying neoplastic prostate cells to inhibit proliferation. The constructs employ the PSE in conjunction with a promoter region, particularly the 541 bp promoter region of the prostate-specific antigen, and a gene encoding a protein which permits selective ablation of prostate cells, particularly neoplastic prostate cells. Treatment of neoplastic cells comprises the introduction of the construct into neoplastic cells for specific ablation of the neoplastic cells.

Exploiting differential gene expression in neoplastic and hyperplastic cells represents one means for selectively killing such abnormal cells. The control of gene expression in various cell types commonly involved in neoplasia has been studied.

Recently, highly specific enhancers/promoters have been identified; that is, DNA sequences to which are bound proteins (e.g., transcription factors) that only exist in certain types of cells and which modulate the transcriptional activity of cis-linked DNA sequences. These enhancer-binding proteins are activators of transcription that regulate the expression of certain genes that are therefore expressed only in these cells and/or become transcriptionally active under certain conditions (e.g., when bound to a specific hormone, then phosphorylated, when certain other proteins are present). A number of transcriptionally active enhancer elements have been reported. Steroid-regulated enhancer elements have been identified and generally bind to ligand-bound steroid receptors (Nawaz et al. (1992) Gene Expr. 2: 39; Allan et al. (1991) 3 Biol. Chem. 266: 5905; Ozono et al. (1991) J. Biol. Chem. 265: 21881; Meyer et al. (1989) Cell 57: 443; Bagchi et al. (1988) Mol. Endocrinol. : 1221; Bradshaw et al. (1988) Mol. Endocrinol. 2 (12): 1286; Weinberger et al. (1987) Clin. Physiol. Biochem. 5: 179). Associated with expression of the prostate specific antigen is an androgen response element at position −175 to −155. A variety of tissue-specific enhancers and promoters have also been identified in numerous tissues, including liver (Rouet et al. (1992) J. Biol. Chem. 267: 20765; Lemaigne et al. (1993) J. Biol. Chem. 268: 19896; Nitsch et al. (1993) Mol. Cell. Biol. 13: 4494), stomach (Kovarik et al. (1993) J. Biol. Chem. 268: 9917), and pituitary gland (Rhodes et al. (1993) Genes Dev. 7: 913), among others.

Palmiter et al. (1987) Cell 50: 435, reports a strategy for using a pancreas-specific elastase I promoter/enhancer linked to a diphtheria toxin gene to form a chimeric transgene which, when introduced into fertilized murine eggs by micro-injection, can be used to generate a transgenic mouse wherein cells which normally express the elastase I gene are selectively deleted as a result of the expression of the diphtheria toxin encoded by the transgene. Similar strategies have also been used to produce transgenic mice lacking growth-hormone expressing cells (Behringer et al. (1988) Genes Dev. 2: 453) and transgenic mice that are deficient in Schwann cells (Messing et al. (1992) Neuron 8: 507).

The prostate-specific antigen (PSA) gene is preferentially expressed in prostate cells and has been cloned (Lundwall A and Lilja H (1987) FEBS Lett 214: 317; Lundwall A (1989) Biochem. Biophys. Res. Commun. 161: 1151; Riegmann et al. (1991) Molec. Endocrinol. 5: 1921).

However, tissue-specific enhancers and promoters which are active in prostate cells, and particularly in neoplastic or hyperplastic prostate cells, would be useful to those in the art, as would constructs suitable for therapeutic ablation of prostate tissue, especially neoplastic prostate epithelium. Therapy based on cell-specific transcriptional regulatory elements would provide a therapeutic modality which likely would be cell-type specific. For such an approach to be used for treating BPH and/or prostate cancer, it would be advantageous to have transcriptional regulatory elements which are preferentially active in prostate acinar cells, from which nearly all metastatic prostate carcinomas arise (Ghadzizadel et al. (1984) Urol. Int. 39: 9). Targeting acinar cells should leave the prostate stromal cells relatively unaffected, and retain the ejaculatory ducts and urethra that pass through it. This would be a significant advantage over present surgical approaches. The present invention fulfills these and other needs. The references discussed herein are provided solely for their disclosure prior to the filing date of the present application. Nothing herein is to be construed as an admission that the inventors are not entitled to antedate such disclosure by virtue of prior invention. All cited publications are incorporated herein by reference.

SUMMARY OF THE INVENTION

In accordance with the foregoing, in one aspect of the invention is provided transcriptional regulatory elements, such as enhancers and promoters, which activate transcription of cis-linked sequences in prostate cells in a tissue-specific manner. Such elements are typically present in or adjacent to genes which are expressed preferentially in prostate cells but substantially not expressed in other cell types.

In one embodiment, the transcriptional regulatory element comprises an enhancer element present in the upstream flanking region of the prostate-specific antigen (PSA) gene, wherein said enhancer activates transcription of cis-linked sequences in prostate cells (e.g., prostate epithelium). In one variation, the transcriptional regulatory element comprises an approximately 5.3 kb fragment of the region immediately upstream of the human PSA gene; this 5.3 kb fragment is frequently isolated as a XbaI-HindIII fragment but restriction site polymorphisms may exist. In another variation, as much or more than 2.5 kp can be deleted internally within the approximately 5.3 kp fragment.

In one aspect of the invention are provided polynucleotides comprising a transcriptional regulatory element that activates transcription of cis-linked sequences in prostate cells such as neoplastic or hyperplastic prostate cells. Typically, such polynucleotides further comprise a structural gene (e.g., a cDNA or genomic gene or minigene)or an antisense sequence operably linked to the transcriptional regulatory element forming a transcription unit. Such a transcription unit generally comprises a structural gene operably linked to a promoter and optionally also a prostate-specific enhancer (i.e., an enhancer element functional in prostate cells but substantially inactive in other cell types). Most usually, the polynucleotides of the invention are used as transgenes and/or homologous targeting constructs and are typically dsDNA constructs.

In one variation, the polynucleotide comprises a transcriptional regulatory element which is expressed preferentially in prostate cells (preferably in neoplastic and/or hyperplastic prostate cells) and which is used to drive the expression of an operably linked toxin gene encoding a cytotoxic or cytostatic gene product. The toxin gene is expressed in prostate cells which have incorporated the polynucleotide, thereby ablating said prostate cells. Delivery of such polynucleotides to neoplastic or hyperplastic prostate cells results in specific ablation of undesired prostate cells for therapy or prophylaxis of benign prostatic hypertrophy, prostate neoplasia, and the like.

In one embodiment, the invention provides a method for treating or preventing benign prostatic hypertrophy and prostate cancer. The method comprises delivering a polynucleotide consisting essentially of toxin gene operably linked to a prostate-specific transcriptional regulatory element (i.e., promoter and/or enhancer) which is/are preferentially transcriptionally active in neoplastic or hyperplastic prostate cells. A preferred transcriptional regulatory element is a segment upstream of the prostate-specific antigen (PSA) gene which confers prostate-specific expression of a cis-linked gene sequence when transfected into cell expressing PSA. The segment of interest is encompassed in an upstream segment from the transcription initiation site of less than about 10 kbp. Commonly, the upstream segment comprises an approximately 6.0, particularly 5.3 kb, segment immediately upstream from the major PSA transcription initiation site, beginning at +16, particularly 0; often the 5.3 kb segment is conveniently isolated as a XbaI-HindIII fragment. In the method, the polynucleotide construct is typically delivered to prostate tissues (e.g., a prostate tumor mass) as dsDNA, either as naked DNA, as DNA-lipid complexes, by viral delivery, or the like.

In a variation of the invention, a prostate-specific transcriptional regulatory element is operably linked to a gene encoding an immunogenic antigen which is highly visible to the immune system (i.e., readily identified by and reacted against by cytotoxic immune cells). Cells expressing the antigen are hereby rendered susceptible to ablation by, for example, natural killer (NK) cells and the like. Frequently, the antigen is a human immunoglobin κV region, SV40 large T antigen, or spike glycoproteins of enveloped viruses (e.g., glycoprotein H of human cytomegalovirus (hCMV). Such polynucleotides can be used to advantage for treating prostate hypertrophy and/or prostatic aplasia by eliciting an immune response against the tumor cells which incorporate and express the cis-linked antigen gene. The invention also provides a method of treating prostatic hypertrophy and prostatic neoplasia by administering a polynucleotide comprising a PSA gene transcriptional regulatory element operably linked to an antigen gene (e. g., immunoglobin κV region, SV40 large T).

In another aspect of the invention are provided polynucleotides comprising prostate-specific gene transcriptional regulatory element operably linked to an gene encoding a lymphokine which activates an anti-tumor immune response (e.g., increased NK activity). Typically, such activating lymphokines include but are not limited to: IL1, IL-2, IL-12, GM-CSF, IFNα, IFNβ, IFNγ, and the like. Frequently, the transcriptional regulatory element is a PSA gene promoter/enhancer. Polynucleotide constructs comprising a prostate-specific gene transcriptional regulatory element operably linked to an activating lymphokine gene are introduced into hypertrophic prostate cells or neoplastic prostate cells whereupon the prostate cells express the lymphokine and thereby enhance an immune reaction against the hypertrophic or neoplastic prostate cells. The invention also provides a method for treating prostate hypertrophy and prostate neoplasia, said method comprising delivering such a polynucleotide construct which expresses an activating lymphokine in prostate cells (e.g., cells expressing PSA). Typically, the step of delivering the polynucleotide construct is accomplished by direct administration of the construct in the form of naked DNA, lipid-DNA complexes, as condensed DNA bound by a polycation and optionally also a ligand for a prostate cell receptor (e.g., FGF receptor), or as viral-packaged DNA. Alternatively, hypertrophic or neoplastic prostate cells can be explanted from a patient, transfected with such a polynucleotide construct, and reintroduced into the patient (typically at the site of explant) to elicit an immune response in the patient against his own prostate tumor.

The invention also provides non-human animals harboring a transgene comprising a prostate-specific transcriptional regulatory element operably linked to a structural gene. Such transgenic animals express the structural gene in prostate cells. Frequently, the prostate-specific transcriptional regulatory element comprises a 5.3 kb immediate upstream region of the human PSA gene, or portions thereof, and the structural gene is expressed in cells which express an endogenous PSA gene. A variety of structural genes can be selected for operable linkage to the prostate-specific promoter/enhancer in the transgene. Advantageously, an activated oncogene or large T antigen gene can be selected as the structural gene, whereupon the transgenic animal can have an increased propensity for developing prostate neoplasia and serve as a disease model for BPH and prostatic carcinoma.

The invention also provides a method for purifying prostate-specific transcription factors, the method comprising contacting cell extracts (typically nuclear extracts) from prostate cells (e.g., a prostate tumor cell line) with DNA comprising a prostate-specific transcriptional regulatory element (e.g., a 5.3 kb segment immediately upstream of the human PSA gene). The step of contacting is typically performed under suitable conditions for specific binding of the transcription factor(s) to the recognition site(s) on the DNA, whereupon unbound material is removed by washing and the retained material containing the transcription factor(s) is recovered. Transcription factors present in prostate tissue and absent in other tissues are identified as prostate-specific transcription factors.

BRIEF DESCRIPTION OF THE FIGURES

FIG. 1 shows the sequence of the 5' flanking region of the human prostate specific antigen to −5824bp. (SEQ ID NO:01). The fragment runs from a HindIII site at −5824 bp to the HindIII site at +7 bp. The numbering system is +1 at the transcription start site of PSA mRNA (Lundwall, A., 1989, Characterization of the gene for Prostate-specific antigen, a human glandular kallikrein. Biochim. Biophys. Res. Commun. 161:1151–1159). The coding region of PSA starts at +42.;

DEFINITIONS

Figures 2, 3:
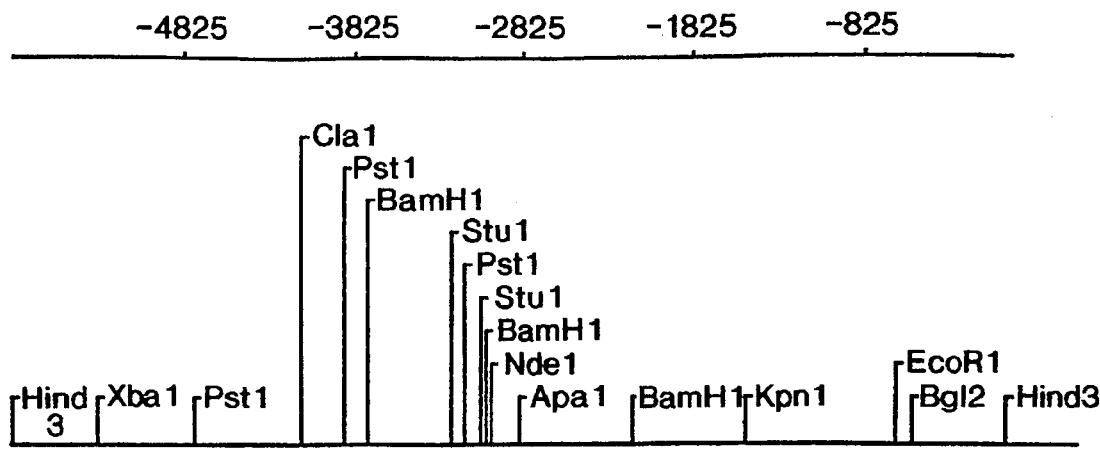
FIG. 2 is a restriction map of the PSA enhancer, extending from the 5' HindIII site to the 3' HindIII site.
FIG. 3 gives the numerical base positions for the cleavage sites for the indicated restriction enzymes.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described. For purposes of the present invention, the following terms are defined below.

The terms "substantially corresponds to", "substantially homologous", or "substantial identity" as used herein denotes a characteristic of a nucleic acid sequence, wherein a nucleic acid sequence has at least about 70 percent sequence identity as compared to a reference sequence, typically at least about 85 percent sequence identity, and preferably at least about 95 percent sequence identity as compared to a reference sequence, often at least 99 percent identical. The percentage of sequence identity is calculated excluding small deletions or additions which total less than 25 percent of the reference sequence. The reference sequence may be a subset of a larger sequence, such as a portion of a gene or flanking sequence, or a repetitive portion of a chromosome. However, the reference sequence is at least 18 nucleotides long, typically at least about 30 nucleotides long, and preferably at least about 50 to 100 nucleotides long. Desirably the extent of similarity between the two sequences will be at least about 80%, preferably at least about 90%, in accordance with the FASTA program analysis. (Pearson and Lipman, Proc. Natl. Acad. Sci. USA (1988) 85:2444–8))

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory is naturally-occurring. As used herein, laboratory strains of rodents which may have been selectively bred according to classical genetics are considered naturally-occurring animals.

As used herein, a "heterologous" is defined in relation to a predetermined referenced gene sequence. For example, with respect to a structural gene sequence, a heterologous promoter is defined as a promoter which does not naturally occur adjacent to the referenced structural gene, but which is positioned by laboratory manipulation. For illustration, an SV40 large T antigen promoter is heterologous with respect to any gene other than large T antigen.

The term "transcriptional enhancement" is used herein to refer to functional property of producing an increase in the rate of transcription of linked sequences that contain a functional promoter.

As used herein, the term "transcriptional regulatory element" refers to a DNA sequence which activates transcription alone or in combination with one or more other DNA sequences. A transcriptional regulatory element can, for example, comprise a promoter, response element, negative regulatory element, and/or enhancer.

As used herein, a "transcription factor recognition site" and a "transcription factor binding site" refer to a polynucleotide sequence(s) or sequence motif(s) which are identified as being sites for the sequence-specific interaction of one or more transcription factors, frequently taking the form of direct protein-DNA binding. Typically, transcription factor binding sites can be identified by DNA footprinting, gel mobility shift assays, and the like, and/or can be predicted on the basis of known consensus sequence motifs, or by other methods known to those of skill in the art. For example and not to limit the invention, eukaryotic transcription factors include, but are not limited to: NFAT, AP1, AP-2, Sp1, OCT-I, OCT-2, OAP, NFKB, CREB, CTF, TFIIA, TFIIB, TFIID, Pit-I, C/EBP, SRF (Mitchell, P. J. and Tijan, R. (1989) Science 245: 371). For purposes of the invention, steroid receptors, RNA polymerases, and other proteins that interact with DNA in a sequence-specific manner and exert transcriptional regulatory effects are considered transcription factors. In the context of the present invention, binding sites for prostate-specific transcription factors (or prostate-specific transcription complexes) are often included in the prostate-specific transcriptional regulatory element (s).

As used herein, the term "operably linked" refers to a linkage of polynucleotide elements in a functional relationship. A nucleic acid is "operably linked" when it is placed into a functional relationship with another nucleic acid sequence. For instance, a promoter or enhancer is operably linked to a coding sequence if it affects the transcription of the coding sequence. Operably linked means that the DNA sequences being linked are typically contiguous and, where necessary to join two protein coding regions, contiguous and in reading frame. However, since enhancers generally function when separated from the promoter by several kilobases and intronic sequences may be of variable lengths, some polynucleotide elements may be operably linked but not contiguous.

As used herein, the term "transcriptional unit" or "transcriptional complex" refers to a polynucleotide sequence that comprises a structural gene (exons), a cis-acting linked promoter and other cis-acting sequences necessary for efficient transcription of the structural sequences, distal regulatory elements necessary for appropriate tissue-specific and developmental transcription of the structural sequences, and additional cis sequences important for efficient transcription and translation (e.g., polyadenylation site, mRNA stability controlling sequences).

Unless specified otherwise, the left-hand end of single-stranded polynucleotide sequences is the 5' end; the left-hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' of the 5' end of the RNA transcript are referred to as "upstream sequences"; sequence regions on the DNA strand having the same sequence as the RNA and which are 3' to the 3' end of the RNA transcript are referred to as "downstream sequences".

As used herein, the term "toxin gene" refers to a polynucleotide sequence which encodes a polypeptide that, when expressed in a eukaryotic cell, typically a mammalian cell, kills the cell or causes the cell to exhibit apoptosis, cytostasis, senescence, or a block in expressing a differentiated function such as expression of a cell-type specific protein, and in one or more of these ways ablates a cell subpopulation. Preferred toxin genes of the invention are: diphtheria toxin A-chain gene (DTA), ricin A chain gene (Ric), herpesvirus thymidine kinase gene (tk), and Pseudomonas exotoxin gene (PE). Other suitable toxin genes will be apparent to those of skill in the art, such as suitable nucleases and proteases that, when expressed intracellularly as gytoplasmic proteins, lead to cell death. Alternatively, toxin genes encoding a defective mutin of an essential cell protein (e.g., a housekeeping gene such as GAPDH) may kill cells by acting as competitive or non-competitive inhibitors of the ognate normal protein (s). Most preferably, the toxin gene is DTA gene.

As used herein, the term "mutein" refers to a nutationally altered biologically active protein that retains the activity of the parent analog but comprises at least one deviation in primary amino acid sequence as compared to the sequence of the parent analog (Glossary of Genetics and gytogenetics, 4th Ed., p.381, Springer-Verlag (1976), incorporated herein by reference). For example but not limitation, a DTA mutein may comprise a primary amino acid sequence having sequence identity to a naturally-occurring DTA polypeptide except at a residue position where a amino acid substitution (typically conservative) has been made, and the DTA mutein possesses cytotoxic activity, albeit not necessarily DTA the same specific activity as naturally-occurring DTA.

DETAILED DESCRIPTION

Generally, the nomenclature used hereafter and the laboratory procedures in cell culture, molecular genetics, and nucleic acid chemistry and hybridization described below are those well known and commonly employed in the art. Standard techniques are used for recombinant nucleic acid methods, polynucleotide synthesis, cell culture, and transgene incorporation (e. g., electroporation, micro-injection, Lipofection). Generally enzymatic reactions, oligonucleotide synthesis, and purification steps are performed according to the manufacturer's specifications. The techniques and procedures are generally performed according to conventional methods in the art and various general references which are provided throughout this document. The procedures therein are believed to be well known in the art and are provided for the convenience of the reader. All the information contained herein is incorporated herein by reference.

Chimeric targeted mice are derived according to Hogan, et al., *Manipulating the Mouse Embryo: A Laboratory Manual*, Cold Spring Harbor Laboratory (1988) and *Teratocarcinomas and Embryonic Stem Cells: A Practical Approach*, E. J. Robertson, ed., IRL Press, Washington, D.C., (1987) which are incorporated herein by reference.

Embryonic stem cells are manipulated according to published procedures (*Teratocarcinomas and Embryonic Stem Cells: A Practical Approach*, E. J. Robertson, ed., IRL Press, Washington, D.C. (1987); Zjilstra et al., *Nature* 342:435–438 (1989); and Schwartzberg et al., *Science* 246:799–803 (1989), each of which is incorporated herein by reference).

Oligonucleotides can be synthesized on an Applied Bio Systems oligonucleotide synthesizer according to specifications provided by the manufacturer.

Methods for PCR amplification are described in the art (*PCR Technology: Principles and Applications for DNA Amplification* ed. H. A. Erlich, Freeman Press, New York, N.Y. (1992); *PCR Protocols: A Guide to Methods and Applications*, eds. Innis, Gelfland, Snisky, and White, Academic Press, San Diego, Calif. (1990); Mattila et al. (1991) *Nucleic Acids Res.* 19: 4967; Eckert, K. A. and Kunkel, T. A. (1991) *PCR Methods and Applications* 1: 17; PCR, eds. McPherson, Quirkes, and Taylor, IRL Press, Oxford; and U.S. Pat. No. 4,683,202, which are incorporated herein by reference).

The existence of tissue/organ-specific transcriptional regulatory elements, e.g. enhancers/promoters, provides the opportunity for targeting anti-cancer agents to the specific organ where cancer has arisen. This can be done by (a) introducing into cells genes that provide for transcription of a product that can result in ablation of the cells in which the product is transcribed, e.g. genes that encode highly toxic proteins and (b) controlling the expression of such genes with highly specific enhancers/promoters. Thus, only cells of one particular site, that in which cancer has arisen, will be killed. The therapeutic ratio could improve from 1.5:1 to 10:1 or more.

Identification of Prostate-Specific Transcriptional Regulatory Elements

DNA sequences within or flanking a gene which is preferentially expressed in prostate cells contain DNA sequence motifs which function to enhance or drive transcription of the cis-linked gene in prostate cells. These sequences are termed prostate-specific transcriptional regulatory sequences. Such sequences are isolated and evaluated for their capacity to enhance or drive transcription of an operably linked reporter gene (e.g., CAT) in prostate cells and substantially not in other cell types. Minimal functional sequences are defined by deletion analysis and/or linker-scanning mutagenesis and the like, followed by assay of transcriptional activity demonstrating transcription in transfected prostate cells but not in other cell types which have also been transfected with minimal reporter constructs.

A preferred prostate-specific transcriptional regulatory element is contained on the approximately 5.3 kb upstream flanking region of the human PSA gene. This 5.3 kb segment typically is represented by a XbaI-HindIII fragment which is isolated from a human genomic clone library probed with a PSA-specific nucleotide probe (e.g., a PSA cDNA sequence). Of particular interest in this fragment is the region from about −5300 to −2800, particularly −5322 to −2851 by itself or in combination with the region −541 to 0, as well as functional fragments thereof, e.g. the transcription factor binding sequences and response elements encompassed therein, individually or in combination.

A prostate-specific transcriptional regulatory element can comprise a promoter and/or enhancer. For example, a PSA enhancer is identified by deletion analysis of the PSA upstream region between −5.3 kb and −2.8 kb (infra), which typically can be isolated from the human genome as a XbaI-ApaI 2.5 kb fragment; this enhancer is termed the "upstream PSA enhancer." Optionally, the naturally-occurring PSA promoter spanning the segment from about −541 to +7, particularly −320 to +7 of the human PSA gene can be included in operable linkage with the upstream PSA enhancer. This region includes an androgen response element. Alternatively, a heterologous promoter can be operably linked to the PSA upstream enhancer and used to drive expression of an operably linked structural gene sequence (e. g., a toxin gene, reporter gene, or other encoding sequence). Various deletions and point mutations can be made to the upstream sequences of the PSA gene, and each variant evaluated for the ability to drive or enhance transcription of a reporter gene (e.g., CAT) in neoplastic prostate cells (e.g., LNCaP) and for substantially lacking expression in non-prostatic cell types (e.g., NIH3T3, HBL100, HT1149, AR42J, NIH OVCAR-3, 293, or DU145, a human prostate cancer cell line that fails to synthesize PSA).

ANTI-PROLIFERATION CONSTRUCTS

Toxin Gene Constructs

The polynucleotide sequence encoding a toxin molecule is operably linked to cis-acting transcriptional regulatory sequences (e.g., promoter, enhancer) of a prostate-specific gene (e.g., PSA), so that the toxin protein is expressed in prostate cells in a manner similar to the expression of the endogenous prostate-specific gene in naturally-occurring prostate cells, preferably neoplastic prostate cells. Thus, it is usually preferable to operably link a toxin-encoding sequence to transcriptional regulatory elements which naturally occur in or near the prostate-specific gene (e.g., PSA gene).

The operable linkage may be formed by homologous sequence targeting to replace the toxin gene downstream of (i. e., towards the carboxy-terminus of the encoded naturally-occurring polypeptide in translational reading frame orientation) a transcriptional regulatory sequence (i. e., a promoter and the additional elements which confer specific cell-type expression) of the endogenous prostate-specific gene.

Alternatively, the operable linkage may be formed exogenously as a transgene, wherein the toxin gene is operably linked to a transcriptional regulatory sequence isolated from an endogenous prostate-specific gene, typically by genomic DNA cloning. In such transgenes, the transcriptional regulatory sequence is at least the minimal sequence(s) required for efficient cell-type specific expression, which generally is at least a promoter and at least about 0.2 kilobase (kb) upstream of the promoter, preferably at least about 1 to 3 kb upstream of the promoter, more preferably at least about 5 kb upstream of the promoter, and frequently at least about 8 or more kb upstream of the promoter. In the case of the PSA gene, at least a functional promoter and the PSA upstream enhancer are combined to confer prostate-specific expression of operably linked structural gene (toxin gene) sequences. Frequently, sequences downstream of the promoter, especially intronic sequences, be included in the transgene constructs (Brinster et 31. (1988) *Proc. Natl. Acad. Sci. (U.S.A.)* 85: 836, incorporated herein by reference). Usually the sequences upstream of the promoter are used contiguously, although various deletions and rearrangements can be employed. Some desired regulatory elements (e.g., enhancers, silencers) may be relatively position-insensitive, so that the regulatory element will function correctly even if positioned differently in a transgene than in the corresponding germline gene. For example, an enhancer may be located at a different distance from a promoter, in a different orientation, and/or in a different linear order. For example, an enhancer that is located 3' to a promoter in germline configuration might be located 5' to the promoter in a transgene. Where convenient, it is preferred that a contiguous segment of genomic DNA sequence spanning the prostate-specific gene and containing as much upstream flanking sequence as convenient (typically at least about 1–10 kb) be used in the transgene or targeting construct, with the toxin gene inserted so as to replace or displace at least the first intron of the gene and to be operably linked to the promoter (s). It is further recognized that a prostate-specific gene may comprise multiple promoters, which may individually be cell type-specific, and it is necessary to operably link the toxin gene to at least one promoter (or other transcriptional element) which confers transcription in prostate (especially neoplastic prostate) cells. Transcriptional elements which confer transcription in non-prostate cells and which are not necessary for efficient transcription in prostate cells may be advantageously deleted from the transgene or targeting construct to provide additional cell-type specificity for ablating prostate cells and minimizing ablation of other cell types.

If the transcription regulatory sequence(s) selected are relatively inefficient in transcribing the toxin gene, it may be desirable to incorporate multiple copies of a transgene or targeting construct to compensate with an enhanced gene dosage of the transgene.

Toxin Genes

The toxin genes may be toxic independently of any ancillary agent or toxic only inconjunction with an ancillary agent. There are numerous natural toxins which result in cell death upon reaching a minimum intracellular concentration. Other toxic agents induce cell death in conjunction with a second agent, but are otherwise benign. Illustrative of this latter protein is thymidine kinase.

Several polynucleotide sequences are suitable for use as a toxin gene in the transgenes and targeting constructs of the invention. Preferred toxin genes are: diphtheria toxin A chain gene (Palmiter et al. (1987) op.cit. and erratum (1990) *Cell* 62: following p.608; Maxwell et al. (1987) *Mol. Cell. Biol.* 7: 1576; Behringer et al. (1988) op.cit.; Messing et al. (1992) op.cit., incorporated herein by reference), ricin A chain gene (Piatak et al. (1988) *J. Biol. Chem.* 263: 4837; Lamb et al. (1985) *Eur. J. Biochem.* 148: 265; Frankel et al. (1989) *Mol. Cell. Biol.* 9: 415, incorporated herein by reference), Pseudomonas exotoxin gene comprising at least domain III or amino acids 400–600 (Hwang et al. (1987) *Cell* 48: 129; Siegall et al. (1989) *J. Biol. Chem.* 264: 14256; Chaudhary et al. (1990) *Proc. Natl. Acad. Sci. (U.S.A.)* 87: 308, incorporated herein by reference), and the HSV tk gene (Zjilstra et al. (1989) *Nature* 342:435; Mansour et al. (1988) *Nature* 336: 348; Johnson et al. (1989) *Science* 245: 1234: Adair et al. (1989) *Proc. Natl. Acad. Sci (U.S.A.)* 86: 4574; Capecchi, M. (1989) *Science* 244:1288, incorporated herein by reference).

The DTA, Ric, and PE act directly to kill cells in which they are expressed. The HSV tk gene requires the presence of a negative selection agent such as gancyclovir to effect toxicity in vivo. Generally, the dosage of gancyclovir is calibrated by generating a standard dose-response curve and determining the dosage level at which a desired level of ablation of prostate cells is observed. Information regarding administration of gancyclovir (GANC) to animals is available in various sources in the art, including human prescribing directions from package inserts. When used in cell culture, a selective concentration of gancyclovir is typically about 1 µM, with about 0.2 µM used for in vitro applications and about 1–5 µM administered for in vivo applications (typically administered over about 24 hours by continuous infusion from an osmotic pump loaded with 125 mg/ml of gancyclovir in aqueous solution).

Various other toxin genes may be used in the discretion of the practitioner and may include mutated or truncated forms of naturally-occurring proteins which competitively or non-competitively inhibit the correct functioning of the naturally-occurring forms and thereby kill the cell. Alternatively, a toxin gene may comprise a polynucleotide that encodes an engineered cytoplasmic variant of a potent nuclease (e.g., RNase A) or protease (e.g., trypsin, chymotrypsin, proteinase K, etc.) which, when expressed as an enzymatically active polypeptide in the cytoplasm of a cell, produces the death of the cell (as determined, for example, by exclusion of Trypan Blue dye). Alternatively, a toxin gene may comprise a gene that, when expressed in a cytotoxic cell type, causes apoptosis (programmed cell death) of that cell type.

Antigen and Lymphokine Genes

For embodiments where a toxin gene is not employed, one variation of the invention comprises forming an expression polynucleotide by operably linking a prostate-specific transcriptional regulatory element with a structural gene encoding a lymphokine or an antigen which potentiates or elicits an immune response directed against cells expressing said lymphokine or antigen. Typically, a DNA segment comprising a PSA upstream enhancer and promoter are operably linked to the structural gene, forming an expression construct. Typical lymphokine genes are exemplified by, but not limited to, the following: IL-I, IL-2, IL-12, GM-CSF, IFNα, IFNβ, and IFNγ. Typical antigen genes are those which are immunogenic and can be exemplified by, for example, immunoglobin κV region and SV40 large T antigen (Watanabe et al. (1993) *J. Immunol.* 151: 2871, incorporated herein by reference). In one embodiment, a DNA-mediated tumor vaccine where a prostate specific enhancer drives a highly visible antigen such as the immunoglobin κV region of human IgG or SV40 T antigen is used to treat prostate neoplasia. Tumor vaccines of this nature can elicit natural killer cells to ablate any remaining tumor cells. Prostate cells expressing PSA would now become immunogenic and visible to the immune system. These therapies can also be delivered as described for transrectal fine needle biopsy (infra).

Anti-sense Sequences

Instead of having a gene encoding a protein, one may have an antisense sequence of at least about 30bp, usually at least about 50bp, having as a target the coding region of an essential gene for the proliferation or viability of the host. Numerous proteins associated with transcription, translation, metabolic pathways, cytostructural genes, or the like may be the target of the antisense. Desirably, the target should be essential, present at relatively low levels, and particularly associated with neoplastic cells. Of particular interest would be transcription factors associated with genes necessary for proliferation, e.g. oncogenes, or cytoskeleton genes, e.g. β-actin and tubulin, etc.

In the usual context, the antisense gene may be synthesized in accordance with conventional ways, using manual synthesis or automated synthesizers. In the context of PCE, the PSE would be operably linked to encode an antisense construct such that the transcription of the antisense would only occur in cells in which the PSE is active.

Transcriptional Regulatory Sequences

Transgenes and expression polynucleotides of the invention comprise a transcriptional regulatory sequence of a prostate-specific gene operably linked to a toxin gene or other structural gene (e. g., activating lymphokine or immunogenic antigen), and targeting constructs of the invention may comprise such a transcriptional regulatory sequence. Suitable transcriptional regulatory sequences are those which confer prostate-specific transcription of the linked toxin gene, although low levels of transcription may occur in other cell types as well so long as such non-prostate cell expression does not substantially interfere with the health and prognosis of patients treated with the transgenes/ expression polynucleotides.

Suitable transcriptional regulatory sequences of the invention generally are derived from or correspond to polynucleotide sequences within or flanking a gene which is preferentially expressed in a neoplastic prostate cell population. Various prostate-specific genes are suitable, and specific genes may be selected at the discretion of the practitioner. For example, genes which have prostate-specific transcriptional regulatory sequences include prostatic acid phosphatase (PAP), and the genes encoding anitgens which are detected by the monoclonal antibodies TURP-27, Leu 7, 7E 11-C5, and PD41 (Wright et al. (1990) The Prostate 17: 301). For many intended purposes, the human PSA gene is the preferred suitable source for obtaining prostate-specific transcription regulatory sequences.

The human PSA gene has been cloned and characterized by sequencing (Lundwall A (1989) op.cit; Riegman et al. (1991) Molec. Endocrinol. 5:1921, incorporated herein by reference). A toxin gene or other structural gene is preferably inserted in operable linkage with the PSA gene upstream enhancer (and optionally including the PSA promoter). The toxin gene (or other structural gene) is positioned to ensure correct transcription and translation according to standard cloning methods in the art. A targeting construct may be produced having recombinogenlc homology regions flanking the toxin gene (or other structural gene) which correspond to the sequences flanking the chosen insertion site, which will be downstream of the transcription start site. A transgene comprising the regulatory sequences identified herein as the PSA upstream enhancer may also be produced, however it may be desirable to include additional sequences upstream or downstream of the PSA upstream enhancer; such sequences can be readily isolated by routine "chromosome walking" screening of a human genomic library.

Decoys

The PSE region may also serve to be used as decoys, where dsDNA is introduced into the target cells by any convenient means as described previously. The dsDNA may be synthesized from naturally occurring nucleotides or unnatural nucleotides, so long as the dsDNA will bind to the target transcription factor. By introducing decoys into the prostate cells, the transcription factors binding to the PSE will be diverted to the decoys, so that PSA and other genes requiring the transcription factor(s) regulating PSA will be diverted. This will serve to identify those genes which are coordinately regulated with PSA and can also serve to modulate the viability and growth of prostate cells.

DNA DELIVERY METHODOLOGIES

A large number of methodologies for DNA delivery have been developed and new ones are continuing to be developed. The presently available methodologies may be divided into three major groups: transfection with a viral vector; fusion with a lipid; and cationic supported DNA introduction. Each of these techniques has advantages and disadvantages, so that the selection of which technique to use will depend upon the particular situation and its demands.

DNA Delivery to Prostate Cells and Prostatic Carcinoma Cells

Delivery of the polynucleotide constructs of the invention to prostate cells, especially neoplastic prostate cells, can be accomplished by any suitable art-known method.

The invention provides methods and compositions for transferring such expression constructs, transgenes, and homologous recombination constructs into cells, especially in vivo for gene therapy of prostate disease. It is also an object of the invention to provide compositions for the therapy of BPH and prostatic neoplastic diseases.

For gene therapy of such diseases to be practicable, it is desirable to employ a DNA transfer method that accomplishes the following objectives: (1) is capable of directing the therapeutic polynucleotides into specific target cell types (e.g., neoplastic cells, prostate cells), (2) is highly efficient in mediating uptake of the therapeutic polynucleotide into the target cell population, and (3) is suited for use in vivo for therapeutic application.

So far, the majority of the approved gene transfer trials in the United States rely on replication-defective retroviral vectors harboring a therapeutic polynucleotide sequence as part of the retroviral genome (Miller et al. (1990) Mol. Cell. Biol. 10: 4239; Kolberg, R. (1992) J. NIH Res. 4: 43; Cornetta et al. (1991) Hum. Gene Ther. 2: 215). The major advantages of retroviral vectors for gene therapy are: the high efficiency of gene transfer into replicating cells, the precise integration of the transferred genes into cellular DNA, and the lack of further spread of the sequences after gene transduction. Major disadvantages include the inability of retroviral vectors to infect nondividing cells, the inherent inability to characterize completely the retroviral vectors used for gene transduction because retroviral vectors cannot be made synthetically but rather must be produced by infected cultured cells, the inability to target distinct cell types selectively, and the potential for undesirable insertional mutagenesis of the host cell genome, among other problems.

Adenoviral vectors have also been described for potential use in human gene therapy (Rosenfeld et al. (1992) Cell 68: 143). Major advantages of adenovirus vectors are their potential to carry larger insert polynucleotide sequences than retroviral vectors, very high viral titres, ability to infect non-replicating cells, and suitability for infecting tissues in situ, especially in the lung. Major disadvantages are the inclusion of many adenovirus genes in the vectors which encode viral proteins that are immunogenic or have other adverse effects (e.g., cytopathic penton proteins), and potential instability of gene expression because the virus does not integrate stably into chromosomal DNA.

Moreover, because of their inherent antigenicity, most gene therapy methods employing viral vectors are ill-suited for multiple administrations, such as may be required to treat chronic diseases such as, for example, cancer.

The other gene transfer method that has been approved for use in humans is physical transfer of plasmid DNA in liposomes directly into tumor cells in situ. Unlike viral vectors which must be propagated in cultured cells, plasmid DNA can be purified to homogeneity and thus reduces the potential for pathogenic contamination. In some situations (e. g., tumor cells) it may not be necessary for the exogenous DNA to stably integrate into the transduced cell, since transient expression may suffice to kill the tumor cells. Liposome-mediated DNA transfer has been described by various investigators (Wang and Huang (1987) *Biochem. Biophys. Res. Commun.* 147: 980; Wang and Huang (1989) *Biochemistry* 28: 9508; Litzinger and Huang (1992) *Biochem. Biophys. Acta* 1113: 201; Gao and Huang (1991) *Biochem. Biophys. Res. Commun.* 179: 280; Felgner W091/17424; WO91/16024). Unfortunately, liposomal compositions usually do not possess specificity for delivering the exogenous DNA to a predetermined cell type; liposomes are generally indiscriminate in fusing to a wide variety of cell types with approximately equal frequency and often require non-physiological pH conditions for efficient fusion.

Immunoliposomes have also been described as carriers of exogenous polynucleotides (Wang and Huang (1987) *Proc. Natl. Acad. Sci.(U.S.A.)* 84: 7851; Trubetskoy et al. (1992) *Biochem. Biophys. Acta* 1131: 311). Immunoliposomes hypothetically might be expected to have improved cell type specificity as compared to liposomes by virtue of the inclusion of specific antibodies which presumably bind to surface antigens on specific cell types. Unfortunately, antibodies frequently are cross-reactive and bind to a variety of proteins bearing cross-reactive epitopes. This might be expected to pose a particular problem when the antibody is raised against a cell surface antigen that is a member of a conserved gene family or a cell surface antigen that contains a conserved sequence present in many other cell surface proteins. Moreover, immunoglobulins which bind cell surface proteins may be inefficiently endocytosed and/or may cause premature disruption of the immunoliposome upon binding antigen, undesirably releasing the exogenous DNA from the immmunoliposome prior to fusion (Ho and Huang (1985) *J. Immunol.* 134: 4035). In addition, immunoliposome-DNA preparations are relatively inefficient for transfection.

Behr et al. (1989) *Proc. Natl. Acad. Sci.(U.S.A.)* 86: 6982 report using lipopolyamine as a reagent to mediate transfection itself, without the necessity of any additional phospholipid to form liposomes. However, lipopolyamines do not impart a predetermined targeting specificity to the exogenous DNA; for the most part, cells are transfected indiscriminately.

Low molecular weight polylysine ("PL") and other polycations have also been described as carriers to promote DNA-mediated transfection into cultured mammalian cells. Zhou et al. (1991) *Biochem. Biophys. Acta* 1065: 8 reports synthesis of a polylysine-phospholipid conjugate, a lipopolylysine comprising PL linked to N-glutarylphosphatidylethanolamine, which reportedly increases the transfection efficiency of DNA as compared to lipofectin, a commercially used transfection reagent.

Unfortunately, a lipopolylysine does not provide satisfactory cell type specificity and it was reported by the authors to be quite inefficient in transforming cells in suspension.

Polylysine molecules conjugated to asialoorosomucoid ("ASOR") (Wu GY and Wu CH (1987) *J. Biol. Chem.* 262: 4429; Wu GY and Wu CH (1988) *Biochemistry* 27: 887; Wu GY and Wu CH (1988) *J. Biol. Chem.* 263: 14621; Wu GY and Wu CH (1992) 3 *Biol. Chem.* 267: 12436; Wu et al. (1991) *J. Biol. Chem.* 266: 14338; and Wilson et al. (1992) *J. Biol. Chem.* 267: 963, WO92/06180; WO92/05250; and WO91/17761) or transferrin (Wagner et al. (1990) *Proc. Natl. Acad. Sci.(U.S.A.)* 87: 3410; Zenke et al. (1990) *Proc. Natl. Acad. Sci.(U.S.A.)* 87: 3655; Birnstiel WO92/13570) have been described; such conjugates have been predicted to afford target-specific delivery of associated DNA to cells which express the appropriate receptor (i.e., asialoglycoprotein receptor or transferrin receptor, respectively). WO91/14696 describes covalently bound conjugates consisting of oligonucleotides in disulfide linkage to a targeting agent that promotes transport across cell membranes for transferring short antisense oligonucleotides into cells. Birnstiel, WO91/17773, describes polycation conjugates comprising a anti-CD4 antibody or a HIV gp120 fragment to confer targeting specificity for CD4+ T cells. Similar methods can be used to specifically deliver DNA to prostate cells expressing a cell surface receptor which may be targeted with a ligand or a specific antibody reactive with the receptor. Although such methods increase the specificity of delivering the exogenous polynucleotides to a particular cell type, these methods often have a low transfection efficiency as compared to lipofection methods.

Liposome mediated transfection is highly efficient and generally not cell type specific, and lipid:DNA complexes rapidly associate with cells of the reticuloendothelial system (Mannino and Gould-Fogerite (1988) *BioTech* 6: 682). Receptor-mediated transfection theoretically should allow any size DNA or RNA to be transfected, however efficiency is affected by lysosomal degradation of nucleic acid. This has necessitated the use of inhibitors of lysosomal degradation, referred to a lysosomotropic agents, which are usually administered to cells contemporaneously (i.e., within about 1–6 hours prior to or subsequent to) transfection. Unfortunately cytotoxicity of most of these agents like chloroquine limits the universal employment of receptor mediated transfection (Dean et al. (1984) *Biochem. J.* 217: 27).

Essentially any suitable DNA delivery method can be used, although it is generally believed that direct physical application of naked DNA comprising the expression construct/transgene to the target cell population (e.g., prostate tumor mass) is believed to be preferred in many cases.

Therapeutic Method for Prostate Hypertrophy and Neoplasia

Prostate cancer and benign prostate hyperplasia can be treated, arrested, or prevented using gene therapy wherein a DNA construct which comprises a prostate-specific transcriptional regulatory element can be delivered to prostate cells for targeted expression of a gene.

The nucleic acid compositions can be stored and administered in a sterile physiologically acceptable carrier, where the nucleic acid is dispersed in conjunction with any agents which aid in the introduction of the DNA into cells. Various sterile solutions may be used for administration of the composition, including water, PBS, ethanol, lipids, etc. The concentration of the DNA will be sufficient to provide a therapeutic dose, which will depend on the efficiency of transport into the cells. Administration may be by syringe needle, trocar, cannula, catheter, etc., as a bolus, a plurality doses or extended infusion, etc. The dose may be administered intralesionally, intravascularly or other appropriate site.

The diphtheria A toxin gene is placed 3' to a prostate-specific enhancer, such as the PSA upstream enhancer. This DNA is delivered by direct injection of the DNA as naked DNA, as a liposome, or other lipofection complex and the like directly into a prostate tumor cell mass in an outpatient procedure analogous to a transrectal fine needle biopsy of the prostate using the Franzen needle. The fine needle biopsy is commonly used for differential diagnosis of BPH and prostate carcinoma as well as staging of prostate carcinoma. The fine needle injection of DNA as a therapeutic can be directed by index finger palpation of nodules, ultrasound, or rectal endoscope. It is possible to repeatedly inject DNA therapeutically with this modality. Frequently, it is preferable that delivery is accomplished by intravenous injection.

The compositions containing the present prostate-specific polynucleotides encoding a toxin or vaccine protein can be administered for prophylactic and/or therapeutic treatments. In therapeutic application, compositions are administered to a patient already affected by the particular neoplastic/ hypertrophic prostate disease, in an amount sufficient to cure or at least partially arrest the condition and its complications. An amount adequate to accomplish this is defined as a "therapeutically effective dose" or "efficacious dose." Amounts effective for this use will depend upon the severity of the condition, the general state of the patient, and the route of administration.

EXPERIMENTAL EXAMPLES

Identification of a Tissue-Specific PSA Upstream Enhancer

The promoter of prostate-specific antigen has been reported (Riegman et al. (1991) op.cit, incorporated herein by reference). The promoter from −320 to +7 contains a TATA-box, a GC-box, and a hormonal response element at −170 to −156. However, transfection of CAT constructs from −1600 to +7 into human prostate LNCaP cells were reportedly unsuccessful. Indeed the functional domains described were found by cotransfecting the CAT constructs into monkey kidney COS cells with an androgen receptor expression plasmid. It was unclear from this work whether the lack of activity of CAT constructs in LNCaP cells was due to poor transfection efficiency or due to a lack of a suitable tissue-specific enhancer element (Reigman et al (1991) op.cit).

Figure 4:
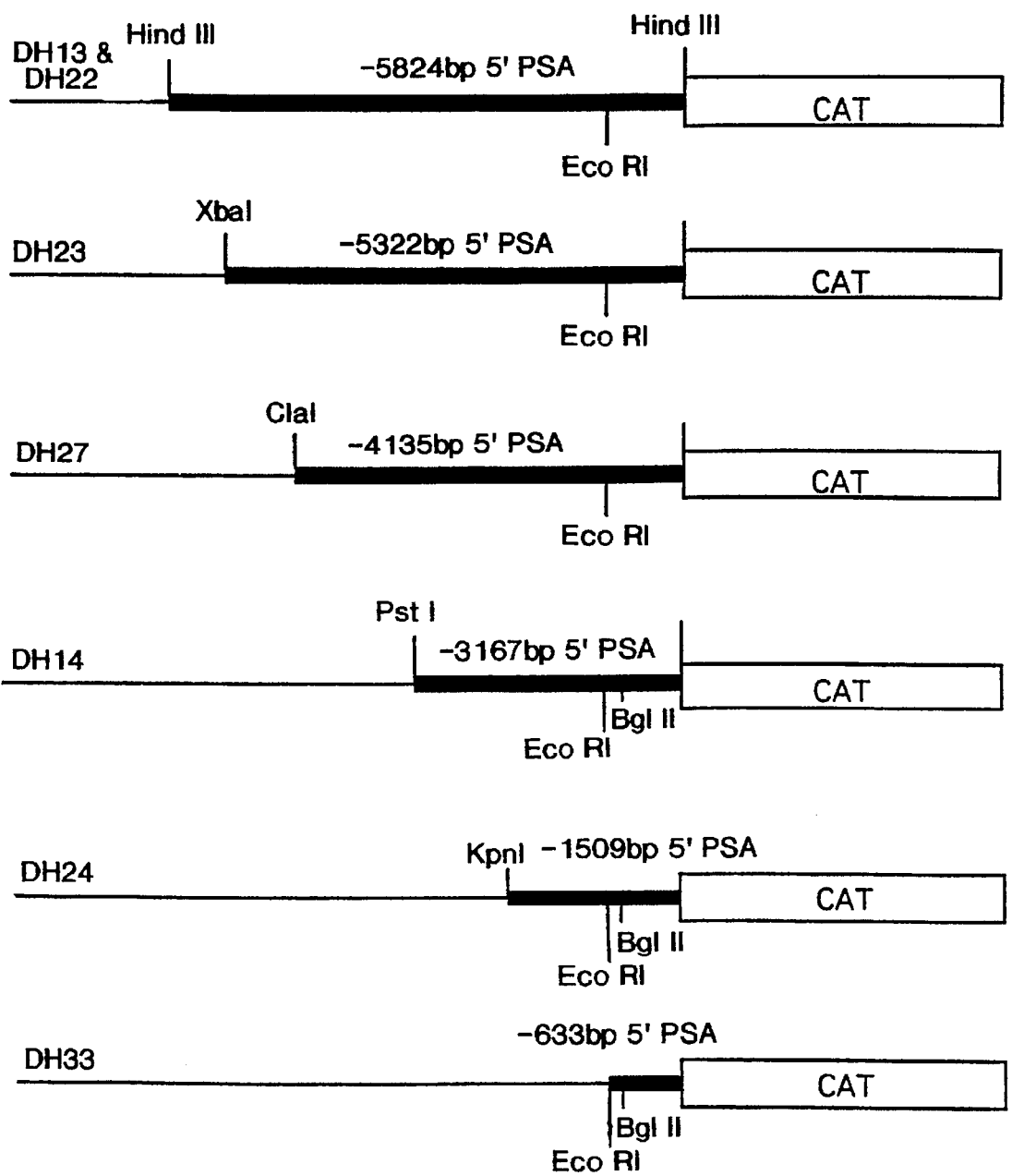
FIG. 4 shows expression constructs wherein various lengths of the region upstream of the human PSA gene are operably linked to a reporter gene, chloramphenicol acetyltransferase (CAT); these constructs were evaluated for transcriptional activity in transfected human prostate LNCaP cells.

A 6 kb fragment representing the 5' flanking region of the prostate specific antigen (PSA) gene which was isolated from a human genomic library in the phage vector Charon 4A was kindly provided by Lundwall (1989) op.cit. This represents a 6 kb fragment in a pUC18 backbone as a HindIII fragment. Restriction digest analysis of the 6 kb 5' flanking region of PSA provided the map of unique sites shown in FIG. 2. The ability of this 6 kb DNA fragment to drive CAT activity was tested by transfection of human prostate LNCaP cells (ATCC). LNCaP cells were plated at a density of 7×10–cells/6 cm dish in 5 ml of RPMI 1640 supplemented with 10% fetal calf serum, 100 U each of penicillin and streptomycin. 24 hrs later cells were washed twice with 2 ml of phosphate buffered saline (PBS) and transfected gently with cationic liposomes. 15 ug of DNA mixed with 30 ug of Lipofectin (Gibco BRL) was added to 3 ml of serum free media/plate. After 24 hrs, the media was removed and replaced with 5 ml of RPMI 1640, 10 FCS. Cells were harvested after an additional incubation of 48 hrs. To prepare extracts, cells were washed twice with PBS, and removed with 1 ml 150 mM NaCl, 50 mM Tris-HCl pH 7.4, 1 mM EDTA. Cells were collected by centrifugation and lysed by 3× freeze-thaw in 100 ul 0.25M Tris-HCl pH 7.4. Following centrifugation at 14,000 RPM, 4° C., 5', the supernatant was removed and stored at −20° C. CAT assays were performed on 50 ug protein of cell extract. The clones shown in FIG. 4 were constructed containing various size deletions of the of the 6 kb 5' flanking region of the PSA gene. Constructs were either in pCAT Basic (Promega) or in pBS KSII+ (Stratagene). Constructs in either plasmid backbone performed substantially identically. To test these constructs, LNCaP cells were transfected with 15 ug DNA/7 ×10–cells in 6 cm dishes with Lipofectin. Lane 1 contained no DNA, lane 2=promoterless CAT, lane 3=−5824 bp 5' PSA CAT, lane 4=−5322 5' PSA CAT, lane 5−4135 bp 5' PSA CAT, lane 6=−3167 bp 5' PSA CAT, lane 6=−1509 bp 5' PSA CAT, lane 7=−633 bp 5' PSA CAT.

Of these constructs only the full −5824 bp HindIII construct and the −5322 bp XbaI construct were found to be capable of driving CAT in human prostate LNCaP cells. Constructs of −4135 bb (a unique ClaI site), or less, were incapable of driving CAT in these cells. Thus, the putative PSA enhancer lies between −5322 bp and −4135 bp: between unique XbaI and ClaI sites. The XbaI-ClaI fragment of about 1.2 kb (SEQ ID NO:02) was transferred to pBSKSII+ and sequenced using primers from the multiple cloning site and then synthesized primers. Both strands of DNA were sequenced using the Sanger dideoxy method. The sequence of this region is shown in the whole sequence of FIG. 1. (SEQ ID NO:01) This region can be conveniently cloned out of a human genomic DNA library or can be amplified by PCR from human genomic DNA, among other methods at the practitioner's discretion.

A computer search of GenBank showed no substantially related sequences to that of FIG. 1.(SEQ ID NO:01).

Prostate specific antigen has enjoyed widespread acceptance as a serum marker for benign hyperplasia and cancer of the prostate. While normal ranges of PSA are from 0 to 4.0 ng/ml, a single measurement of serum PSA levels is not prognostic of a disease condition. However, repeated measurements showing rising levels of PSA over 10 mg/ml and rapid rises within months are cause for serious concern. Such indications are followed by biopsy to determine if the rising PSA levels are due to benign hyperplasia, or prostate cancer. PSA has been shown to be synthesized exclusively in prostate tissue or metastases of neoplastic prostate tissue. Interestingly, to date all metastases of prostate cancer and primary cultures of prostate tissue synthesize PSA (Ghazizadeh et al. (1984) Urol. Int. 39: 9). Of great interest is the question of whether this putative PSA enhancer is tissue-specific. Specifically, does the enhancer direct CAT expression only in prostate tissues and not in other tissues? Table I shows in vitro transfection data of a variety of cell lines with the −6.0 kb 5' PSA flanking sequence driving CAT. LnCaP cells were transfected with Lipofectin. All other cells were transfected by the DEAE-dextran method.

TABLE I

Tissue Specificity of PSA Enhancer

| Cell Line | | CAT Activity |
|---|---|---|
| human cancer prostate | LNCaP | + |
| mouse fibroblast | NIH3T3 | — |
| rat pancreas | AR42J | — |
| human kidney | 293 | — |
| human cancer ovary | NIH OVCAR-3 | — |
| human breast cancer | HBL100 | — |
| human cancer prostate | DU145 | — |
| human bladder cancer | HT1149 | — |

All transfections were negative for promoter less CAT and positive for CAT driven by the SV40 early promoter (SVCAT) with the exception of LNCaP which was also negative for SVCAT. The data in Table I show the putative PSA enhancer to be tissue-specific for prostate tissue that is actively expressing prostate specific antigen. It is interesting to note that DU145, a human prostate tumor line that does not express PSA, also fails to drive CAT from the PSA enhancer. However, tissue-specific expression of PSA is pathognomonic for BPH and prostate cancer questioning the value of PSA negative cell lines for the study of prostate disease. The bladder cell line was chosen since embryologically bladder is the closest relative of the prostate.

The PSA upstream prostate-specific enhancer can be used to form toxin gene expression polynucleotides for cytotoxic therapy of the prostate, for tumor vaccines of the prostate, as well as injection of gene delivery vehicle to target tumor metastases occurring in lymph nodes and bone.

Nude Mice Harboring Prostate-Specific Transgene

Traditionally, in vivo tissue-specificity of enhancers has been shown in transgenic mice. However, the construction of transgenic mice is only conclusive for enhancers which are functional in the mouse. To test the in vivo tissue specificity of the PSA upstream enhancer, a transgene comprising the human PSA upstream enhancer operably linked to the CAT gene driven by a heterologous promoter was injected into nude mice carrying the human prostate tumor LNCaP. 3–4 week-old male nude mice were injected subcutaneously in the back of the neck with 0.5 ml containing 0.25 ml Matrigel (Collaborative Biomedical) and 0.25 ml Dulbecco's MEM without fetal calf serum or antibiotics and containing 1×10$^6$ LNCaP cells at 4° C. Large tumors of about 0.5 to 1.0 grams developed within 4–5 weeks. Mice carrying tumors were injected I.V. into the tail vein with 100 µl containing 100 µg of a DNA expression construct including the PSA upstream enhancer and PSA promoter driving the CAT gene, 0.5% dextrose, and 800 ng of DDAB/DOPE (dimethyldioctadecylammonium bromide/dioleoylphosphatidyl-ethanolamine) (1:2) cationic liposomes.

Figure 12:
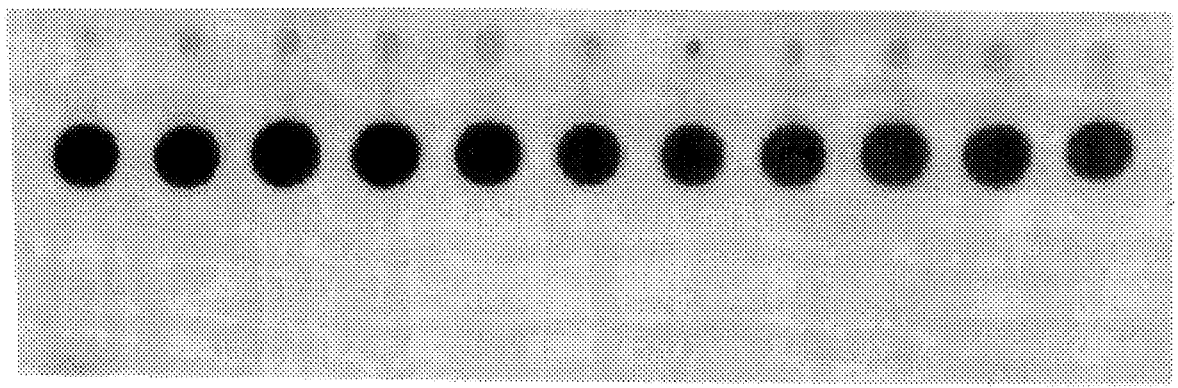
FIG. 12 shows the results of assaying CAT activity in tissue extracts from a nude mouse harboring a human prostate tumor administered a polynucleotide encoding CAT under the transcriptional control of the human PSE. CAT activities from kidney, heart, prostate, liver, pancreas, spleen, brain, lung, bone marrow, bladder and human prostatic tumor mass are shown.

Mice were sacrificed by $CO_2$ suffocation 24 hours later and dissected. Tissues harvested were: kidney, heart, prostate, liver, pancreas, spleen, brain, lung, bone marrow, bladder, and the tumor mass. Tissues were frozen on dry ice and stored at minus 70° C. Tissues (0.025 to 0.25g) were broken in a ground glass Dounce homogenizer in 500–1000 µl 0.25 M Tris pH 7.4, subjected to 3× freeze-thaw, and centrifuged at 14,000 rpm at 4° C. in a microfuge. The supernatant was removed, assayed for protein, and 50 µg protein used for CAT analysis. FIG. 12 shows the results of the CAT assays. The results show CAT activity only in the LNCaP tumors, but no substantial activity in other tissues.

The results are consistent with the PSA upstream enhancer being specific to human prostate tissue. The LNCaP line is a human prostate tissue culture cell line producing PSA. The in vitro cell culture results (supra) also demonstrate that the PSA upstream enhancer is specific for human prostate tissue expressing PSA. Mouse prostate tissue may lack the capacity to recognize the human PSA upstream enhancer. It is interesting to note that mouse prostate, and the embryologically related bladder, failed to synthesize CAT under the tested conditions. The in vitro and in vivo results are consistent with the human PSA upstream enhancer being capable of directing gene expression only in human cells expressing PSA. Therefore, the enhancer can be used to ablate PSA-expressing cells with the gene therapy compositions and methods described herein (supra).

Toxin Construct and Introduction into Prostate Cells

Figure 11:
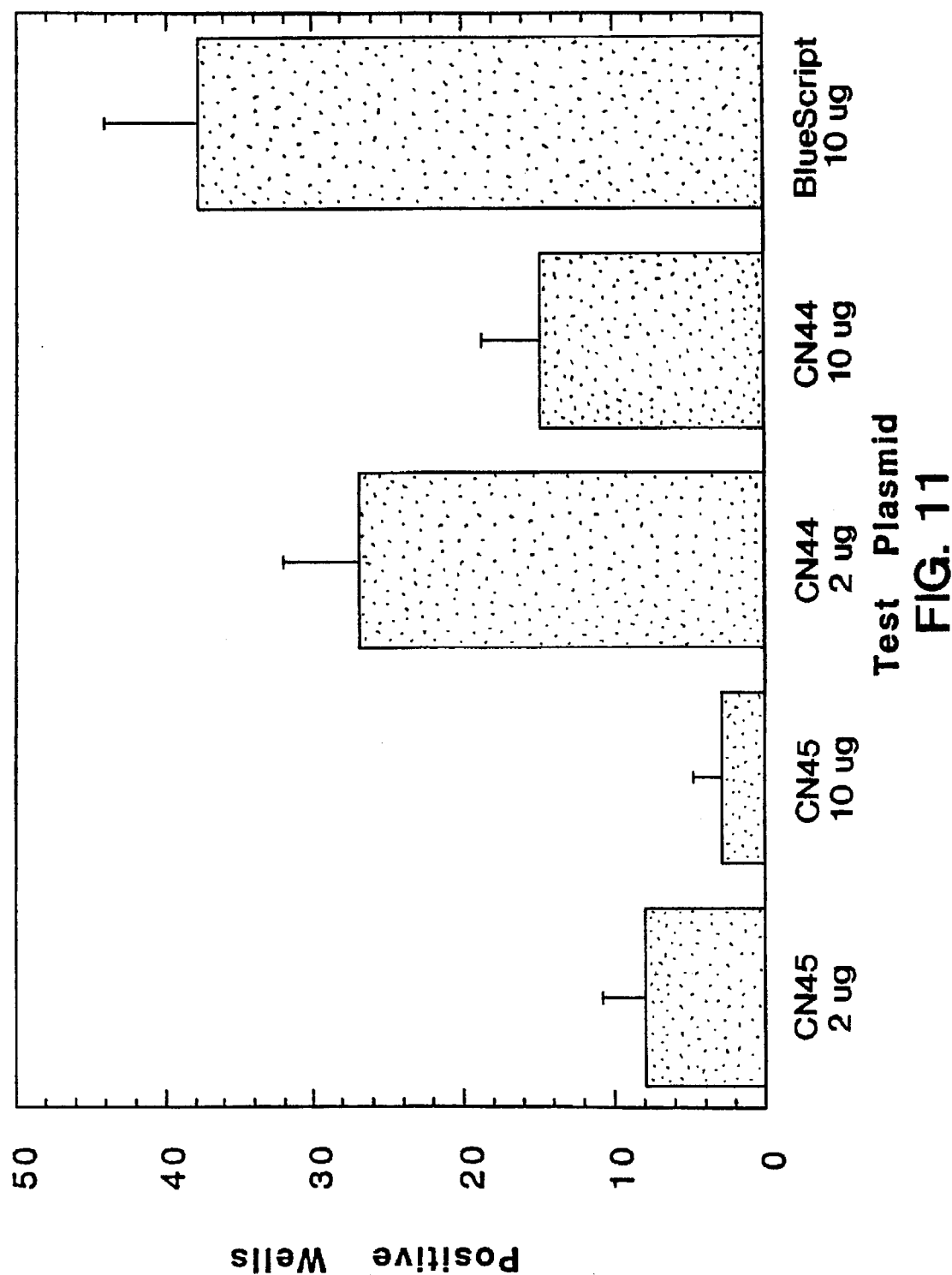
FIG. 11 is a bar diagram showing the in vitro toxicity of the CN45 construct in LNCaP cells. At 15 ug of CN45 DNA in the original transfection 9 colonies grew out. In comparison, BKSKII+ grew out 19 colonies and CN47 grew out 29 colonies. Thus, the presence of a functional diphtheria toxin-A chain in cells co-transfected with a neo expressing plasmid reduced the number of colonies recovered 2–3 fold.

A construct was prepared comprising the diphtheria toxin A subunit (DT-A) (540 bp) 5' to the SV40 t antigen, splice site, and poly A signal in BSKSII+. A triple stop translation codon was placed at the 5' end of the DT-A gene. This clone was designated CN47. The HindIII fragment of the PSE (−5815 to +16) was then cloned upstream of the DT-A gene, and designated CN45. Western blots of polyclonal antibody to diphtheria toxin were positive for expression from CN45. Specifically, the DT-A portion of these constructs were transferred to prokaryotic expression vectors driven by the lac promoter. Following induction with IPTG, preparation of a lysate, gel electrophoresis, and blotting with antibody, CN45 gave a single band of 22,500 MW, the expected size of the DT-A subunit. Both CN45 and CN47 constructs were used to cotransfect LNCaP cells with the plasmid pcDNA3 (Invitrogen) in microtiter plates. pcDNA3 contains the neomycin gene neo, driven by the SV40 early promoter. 48 hours following co-transfection the cells were removed with trypsin and diluted to 10$^5$ cells/mi. 100 ul of each cell suspension was added to each well of a 96-well microtiter plate and incubated for 24 h. The media was removed and replaced with fresh media containing G418 (500 ug/ml). Cells were incubated for 4 weeks with biweekly changes of G418 medium. Positive clones were identified with an XXT assay. The results are reported in FIG. 11.

CAT and LUC Constructs Mapping the 5' PSA Region

Figure 5:
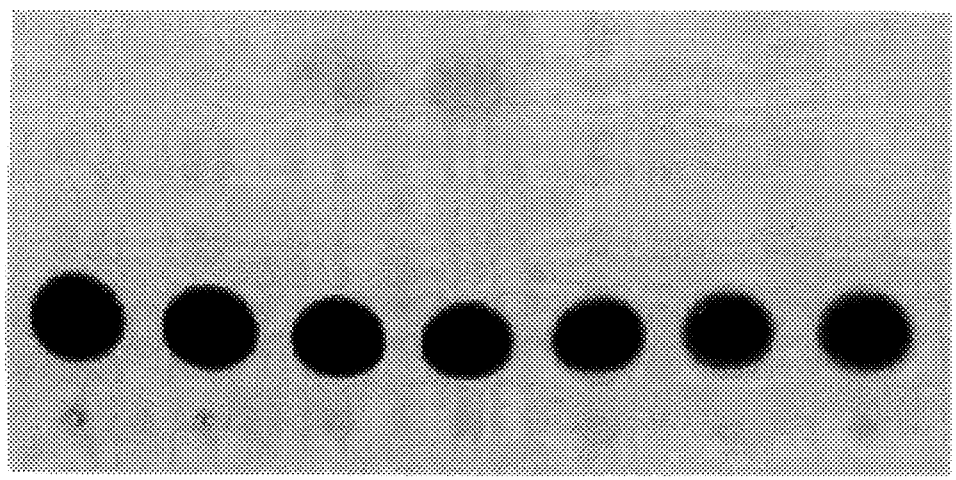
FIG. 5 shows an autoradiogram of the CAT assays of extracts from the prostate cells transfected with the expression constructs shown in FIG. 4.
Figure 6:
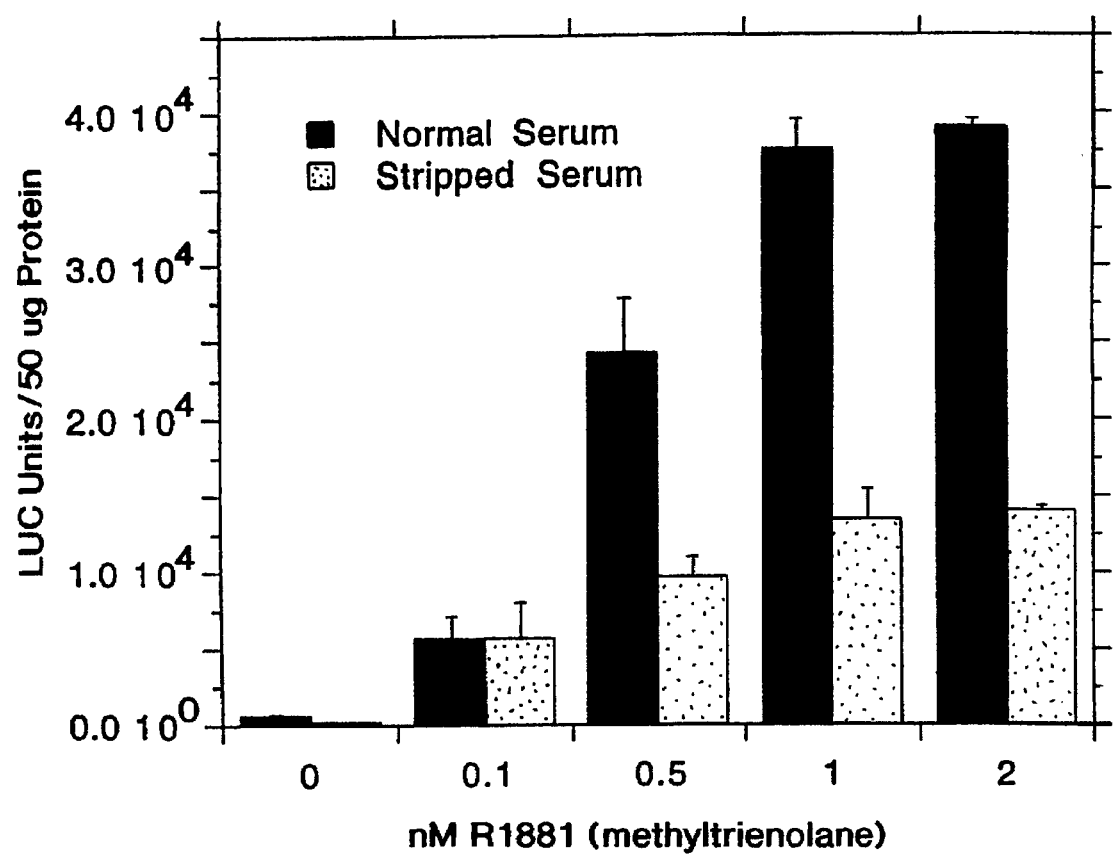
FIG. 6 shows the results of the transfection of LNCaP cells with the entire −5824bp fragment of the 5' flanking region of the PSA gene driving the luciferase gene (LUC) with normal and stripped serum in the presence of increasing amounts of methyltrienolane (R1881).
Figure 7:
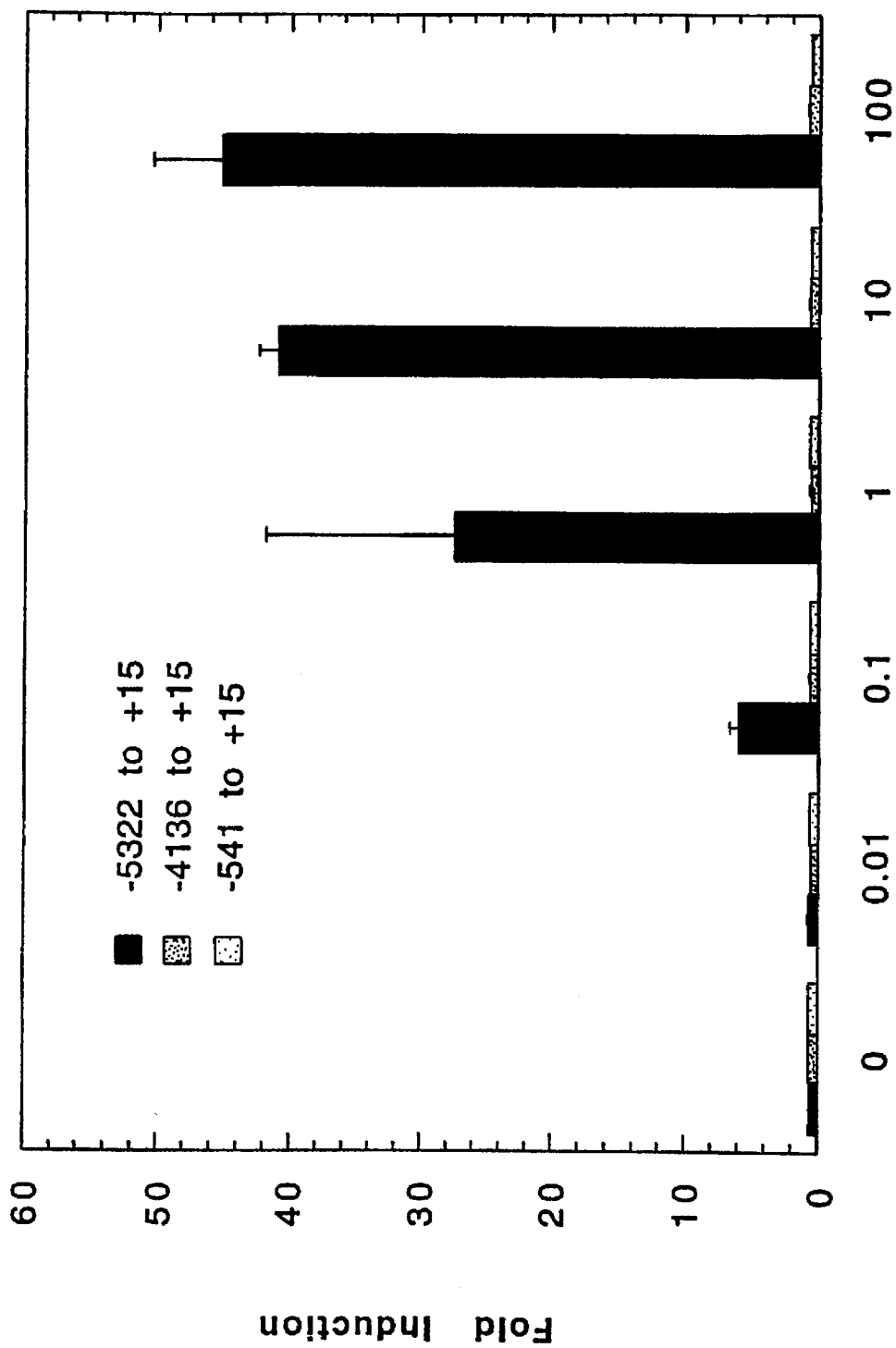
FIG. 7 shows the effect of increasing R1881 concentrations in stripped serum using several constructs of the 5' flanking prostate specific enhancer (PSE) driving CAT.
Figure 8:
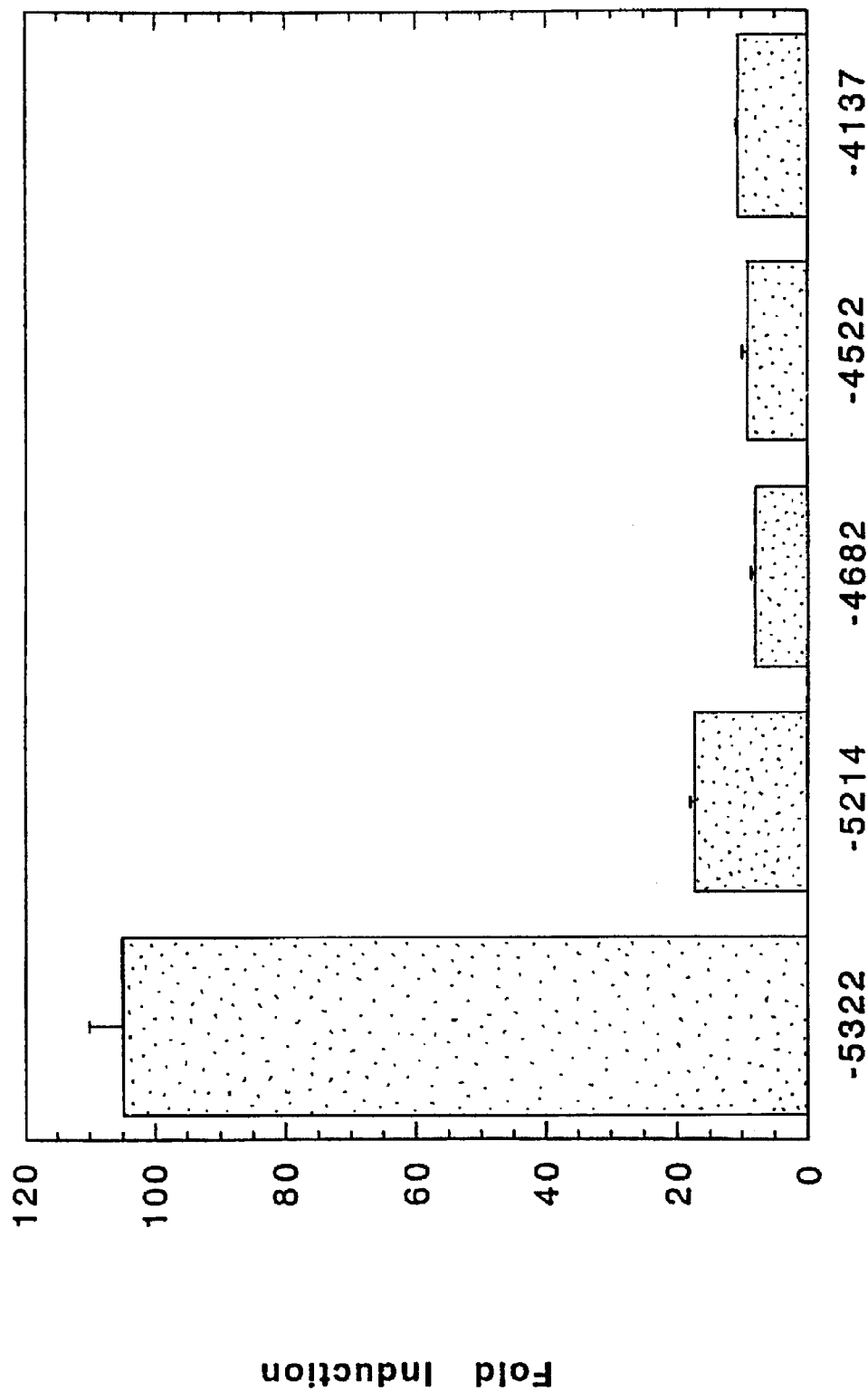
FIG. 8 shows the effect of small deletions designed to define the 5' extent of the required PSE sequence. Constructs were prepared with Exonuclease III in CN42, a construct that contains the XbaI 5' (−5322) to HindIII 3' (+7) end driving the CAT gene in a BSKSII backbone, and sequenced. As seen from FIG. 8, even a small deletion 3' from the XbaI site (108bp) inactivates the PSE.
Figure 9:
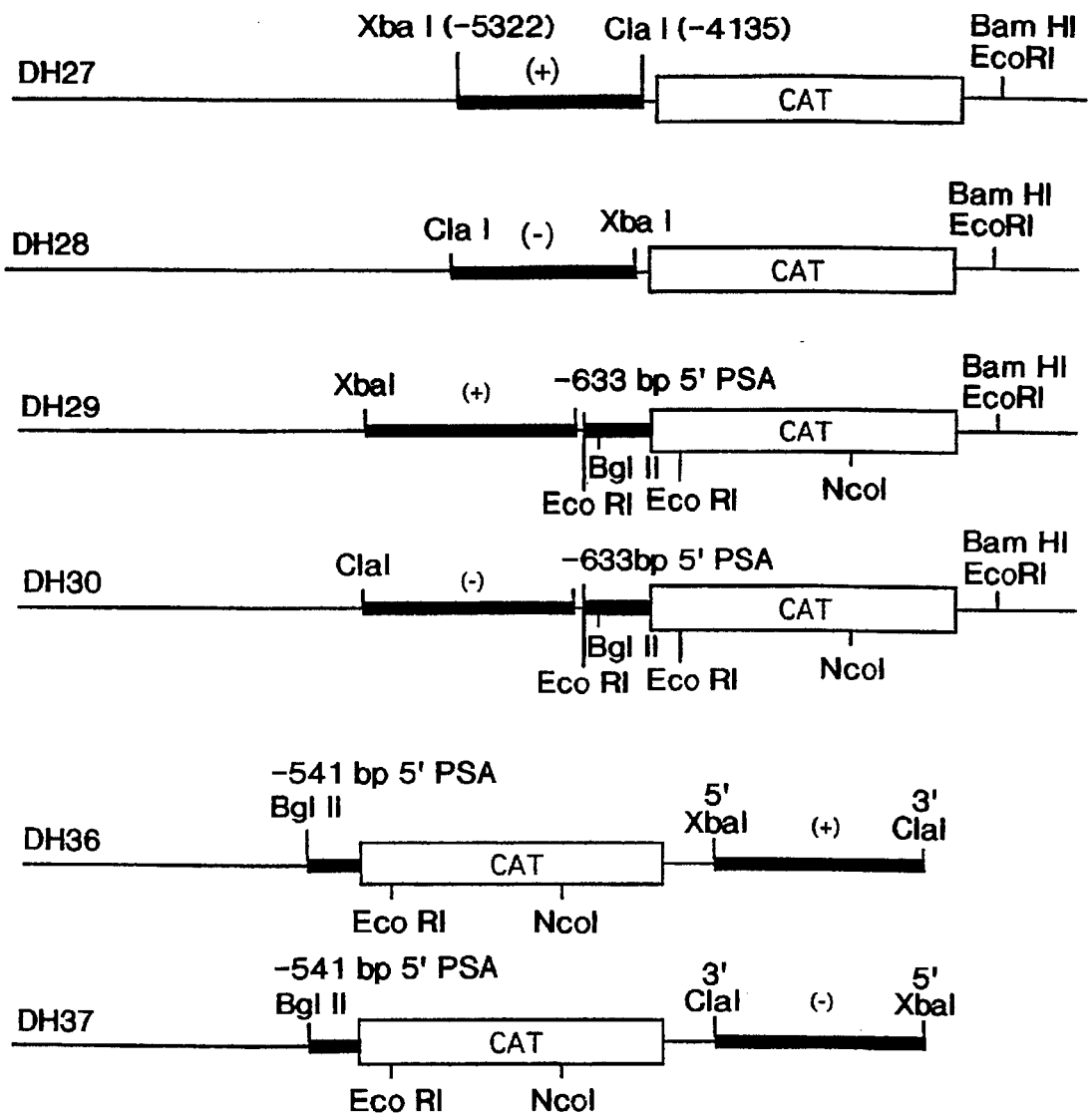
FIG. 9 shows expression constructs where the XbaI-ClaI fragment (SEQ ID NO:02) is moved to various positions in relation to the promoter and coding regions to determine the effect of position of the fragment on its regulatory activity. The 1196bp XbaI - ClaI fragment was moved close to the start site with and without a promoter region in both (+) and (−) orientations, and moved to the 5' end of the CAT gene in both (+) and (−) orientations. None of these constructs showed activity in transfections of LNCaP cells. The conclusion is that the enhancer region within the XbaI (−5322bp) to ClaI (−4135) is required, but it is not sufficient to function as an enhancer. Rather another sequence between the ClaI (−4135) and the HindIII (+7) is required.
Figure 10:
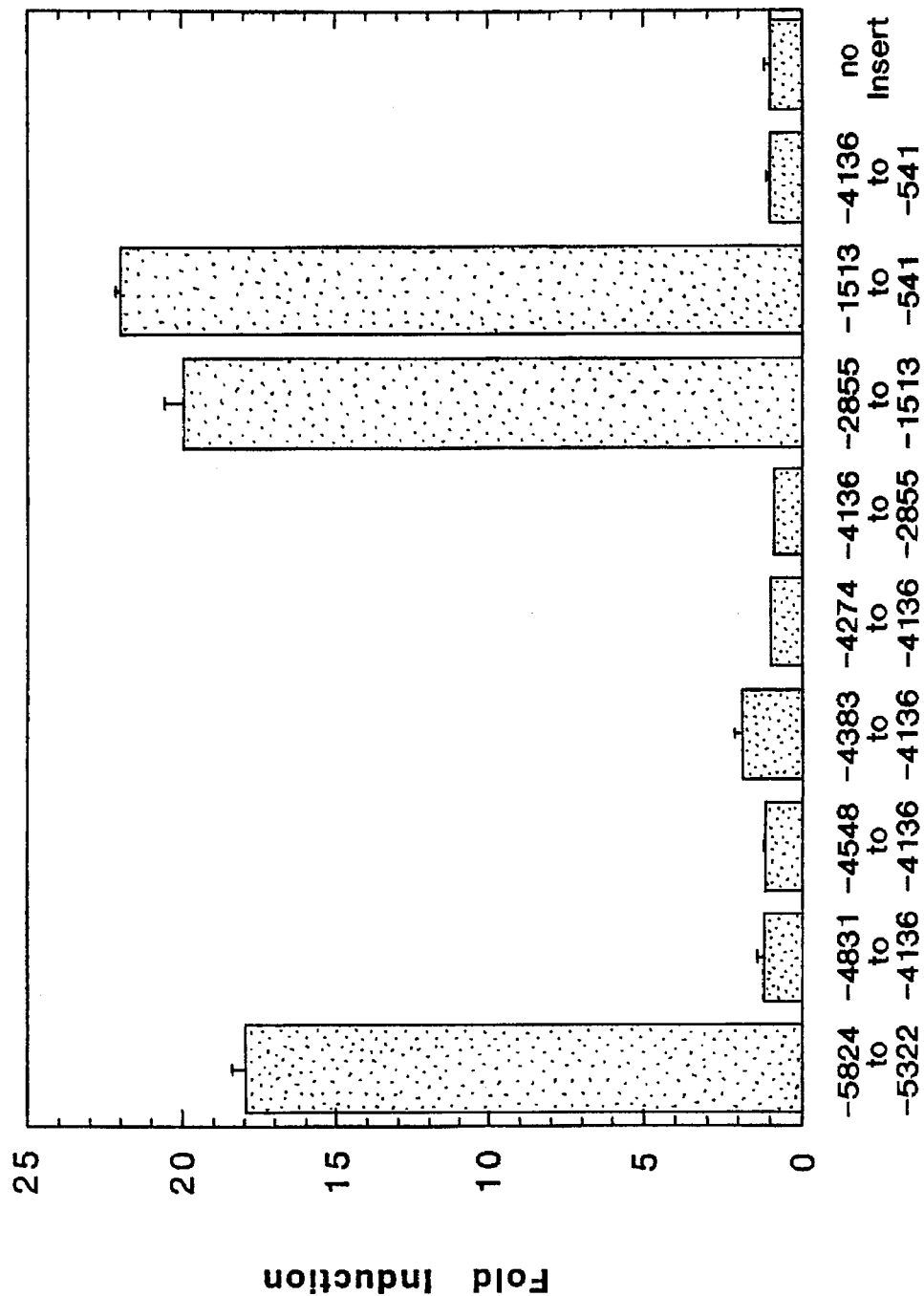
FIG. 10 is a bar diagram of the effect of internal deletions with the PSE driving the CAT gene. The results show that 2310bp, from the ApaI (−2851) to the BglII (−541) can be deleted. Therefore, the additional sequence required for enhancement is located between the ClaI site and the ApaI site. Thus, the entire PSA enhancer is located between the XbaI (−5322) and the ApaI (−2851), a fragment of 2471bp. The enhancer functions in concert with a promoter region that extends from the BglII (−541) site to the start of transcription.

CAT and LUC constructs were prepared by standard molecular biology techniques (Sambrook et al., Molecular Cloning: A laboratory manual, Cold Spring Harbor Laboratories, Cold Spring Harbor, N.Y., 1989) in Bluescript KS+ (Stratagene). LNCaP cells were grown in RPMI supplemented with 10% FCS, and antibiotics (100 U penicillin and 100 U streptomycin/ml). 5–7×10$^6$ were seeded into 6 cm dishes and grown overnight in RPMI, antibiotics, and 10% stripped serum (Gemini). Cells were washed 2× with 2 ml each PBS and transfected with 25 uM DNA complexed with 50 uM DOTMA:DOPE (1:1) in 1 ml RPMI. DOTMA was synthesized with slight modification of the method of Felgner et al.(Proc. Natl. Acad. Sci. USA 84:7413–7417) and DOPE was from Avanti Polar Lipids (Alabaster, Ala.). Cells were incubated for 3 h, the transfection mix was removed and replaced with RPMI with antibiotics, 10% stripped serum and the indicated concentration of the non-metabolizable synthetic testosterone analog R1881 (New England Nuclear). 48 h post-transfection, the cells were washed twice with PBS and removed with 1 ml of TEN. Cell pellets were redissolved in 100 ul of 0.25M Tris (pH 7.8), subjected to 3× freeze-thaw, and debris removed by centrifugation (10,000 RPM, 5') in an Eppendorf Microfuge. The cell extract was assayed for protein by dye binding (Bio-Rad, Richmond, Calif.). For CAT assays, 50 ug protein was made to 50 ul with 0.25M Tris (pH 7.8) and added to 80 ul of a standard CAT assay mix. After 2 h at 37° C. the mix was extracted with 200 ul of TMPD; mixed xylenes (2:1), vortexed for 20 sec, centrifuged at 10,000 RPM for 5', and 180 ul removed for counting by liquid scintillation. For LUC assays, 50 ug protein was made to 50 ul with 0.25M Tris (pH 7.8) and assayed for LUC activity with a Monolight Luminometer 2010 (Analytical Luminescence Laboratory, San Diego, Calif.). The results are reported in FIGS. 5 to 7.

Polynucleotide Delivery

A polynucleotide construct delivery vehicle can be used for intravenous injection to target lymph node and bone metastases of prostate cancer. In this form, the DNA is condensed and coated with poly-L-lysine to which has been attached a natural ligand for a prostate receptor, such as bFGF. Such structures were found to elicit gene expression preferentially within pancreatic cells. In addition, poly-L-lysine attached to βFGF can be mixed with DNA at levels too low to elicit DNA condensation, and optionally mixed with cationic liposomes at concentrations suitable for DNA condensation and uptake into cells. Such cells can bind specifically to cell surface receptors and deliver the DNA to cells bearing the targeted cell surface receptor.

Although the present invention has been described in some detail by way of illustration for purposes of clarity of understanding, it will be apparent that certain changes and modifications may be practiced within the scope of the claims.

What is claimed is:

1. An isolated DNA molecule consisting of the nucleotide sequence from 503 to 2974 of SEQ ID NO: 1.

2. An isolated polynucleotide comprising (1) the nucleotide sequence from 503 to 2974 of SEQ ID NO: 1, and (2) the prostate-specific antigen promoter operably linked to a structural gene other than prostate-specific antigen.

3. An isolated polynucleotide according to claim 2, wherein said structural gene is a toxin gene.

4. An isolated polynucleotide according to claim 2, wherein said polynucleotide is complexed with a liposome.

5. A viral vector comprising the isolated polynucleotide of claim 2.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 5836 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:1:

```
AAGCTTCTAG  TTTTCTTTTC  CCGGTGACAT  CGTGGAAAGC  ACTAGCATCT  CTAAGCAATG     60

ATCTGTGACA  ATATTCACAG  TGTAATGCCA  TCCAGGGAAC  TCAACTGAGC  CTTGATGTCC    120

AGAGATTTTT  GTGTTTTTTT  CTGAGACTGA  GTCTCGCTCT  GTGCCAGGCT  GGAGTGCAGT    180

GGTGCAACCT  TGGCTCACTG  CAAGCTCCGC  CTCCTGGGTT  CACGCCATTC  TCCTGCCTCA    240

GCCTCCTGAG  TAGCTGGGAC  TACAGGCACC  CGCCACCACG  CCTGGCTAAT  TTTTTTGTAT    300

TTTTAGTAGA  GATGGGGTTT  CACTGTGTTA  GCCAGGATGG  TCTCAGTCTC  CTGACCTCGT    360

GATCTGCCCA  CCTTGGCCTC  CCAAAGTGCT  GGGATGACAG  GCGTGAGCCA  CCGCGCCTGG    420

CCGATATCCA  GAGATTTTTT  GGGGGGCTCC  ATCACACAGA  CATGTTGACT  GTCTTCATGG    480

TTGACTTTTA  GTATCCAGCC  CCTCTAGAAA  TCTAGCTGAT  ATAGTGTGGC  TCAAAACCTT    540

CAGCACAAAT  CACACCGTTA  GACTATCTGG  TGTGGCCCAA  ACCTTCAGGT  GAACAAAGGG    600

ACTCTAATCT  GGCAGGATAT  TCCAAAGCAT  TAGAGATGAC  CTCTTGCAAA  GAAAAAGAAA    660

TGGAAAAGAA  AAAGAAAGAA  AGGAAAAAAA  AAAAAAAAAA  GAGATGACCT  CTCAGGCTCT    720

GAGGGAAAC   GCCTGAGGTC  TTTGAGCAAG  GTCAGTCCTC  TGTTGCACAG  TCTCCCTCAC    780

AGGGTCATTG  TGACGATCAA  ATGTGGTCAC  GTGTATGAGG  CACCAGCACA  TGCCTGGCTC    840

TGGGGAGTGC  CGTGTAAGTG  TATGCTTGCA  CTGCTGAATG  CTTGGGATGT  GTCAGGGATT    900

ATCTTCAGCA  CTTACAGATG  CTCATCTCAT  CCTCACAGCA  TCACTATGGG  ATGGGTATTA    960

CTGGCCTCAT  TTGATGGAGA  AAGTGGCTGT  GGCTCAGAAA  GGGGGGACCA  CTAGACCAGG   1020

GACACTCTGG  ATGCTGGGGA  CTCCAGAGAC  CATGACCACT  CACCAACTGC  AGAGAAATTA   1080
```

| | | | | | |
|---|---|---|---|---|---|
| ATTGTGGCCT | GATGTCCCTG | TCCTGGAGAG | GGTGGAGGTG | GACCTTCACT | AACCTCCTAC 1140 |
| CTTGACCCTC | TCTTTTAGGG | CTCTTTCTGA | CCTCCACCAT | GGTACTAGGA | CCCCATTGTA 1200 |
| TTCTGTACCC | TCTTGACTCT | ATGACCCCCA | CTGCCCACTG | CATCCAGCTG | GGTCCCCTCC 1260 |
| TATCTCTATT | CCCAGCTGGC | CAGTGCAGTC | TCAGTGCCCA | CCTGTTTGTC | AGTAACTCTG 1320 |
| AAGGGGCTGA | CATTTTACTG | ACTTGCAAAC | AAATAAGCTA | ACTTTCCAGA | GTTTTGTGAA 1380 |
| TGCTGGCAGA | GTCCATGAGA | CTCCTGAGTC | AGAGGCAAAG | GCTTTTACTG | CTCACAGCTT 1440 |
| AGCAGACAGC | ATGAGGTTCA | TGTTCACATT | AGTACACCTT | GCCCCCCCCA | AATCTTGTAG 1500 |
| GGTGACCAGA | GCAGTCTAGG | TGGATGCTGT | GCAGAAGGGG | TTTGTGCCAC | TGGTGAGAAA 1560 |
| CCTGAGATTA | GGAATCCTCA | ATCTTATACT | GGGACAACTT | GCAAACCTGC | TCAGCCTTTG 1620 |
| TCTCTGATGA | AGATATTATC | TTCATGATCT | TGGATTGAAA | ACAGACCTAC | TCTGGAGGAA 1680 |
| CATATTGTAT | CGATTGTCCT | TGACAGTAAA | CAAATCTGTT | GTAAGAGACA | TTATCTTTAT 1740 |
| TATCTAGGAC | AGTAAGCAAG | CCTGGATCTG | AGAGAGATAT | CATCTTGCAA | GGATGCCTGC 1800 |
| TTTACAAACA | TCCTTGAAAC | AACAATCCAG | AAAAAAAAG | GTGTTGCTGT | CTTTGCTCAG 1860 |
| AAGACACACA | GATACGTGAC | AGAACCATGG | AGAATTGCCT | CCCAACGCTG | TTCAGCCAGA 1920 |
| GCCTTCCACC | CTTGTCTGCA | GGACAGTCTC | AACGTTCCAC | CATTAAATAC | TTCTTCTATC 1980 |
| ACATCCTGCT | TCTTTATGCC | TAACCAAGGT | TCTAGGTCCC | GATCGACTGT | GTCTGGCAGC 2040 |
| ACTCCACTGC | CAAACCCAGA | ATAAGGCAGC | GCTCAGGATC | CCGAAGGGGC | ATGGCTGGGG 2100 |
| ATCAGAACTT | CTGGGTTTGA | GTGAGGAGTG | GGTCCACCCT | CTTGAATTTC | AAAGGAGGAA 2160 |
| GAGGCTGGAT | GTGAAGGTAC | TGGGGAGGG | AAAGTGTCAG | TTCCGAACTC | TTAGGTCAAT 2220 |
| GAGGGAGGAG | ACTGGTAAGG | TCCCAGCTCC | CGAGGTACTG | ATGTGGGAAT | GGCCTAAGAA 2280 |
| TCTCATATCC | TCAGGAAGAA | GGTGCTGGAA | TCCTGAGGGG | TAGAGTTCTG | GGTATATTTG 2340 |
| TGGCTTAAGG | CTCTTTGGCC | CCTGAAGGCA | GAGGCTGGAA | CCATTAGGTC | AGGGTTTGG 2400 |
| GGTGATAGTA | ATGGGATCTC | TTGATTCCTC | AAGAGTCTGA | GGATCGAGGG | TTGCCCATTC 2460 |
| TTCCATCTTG | CCACCTAATC | CTTACTCCAC | TTGAGGGTAT | CACCAGCCCT | TCTAGCTCCA 2520 |
| TGAAGGTCCC | CTGGGCAAGC | ACAATCTGAG | CATGAAAGAT | GCCCAGAGG | CCTTGGGTGT 2580 |
| CATCCACTCA | TCATCCAGCA | TCACACTCTG | AGGGTGTGGC | CAGCACCATG | ACGTCATGTT 2640 |
| GCTGTGACTA | TCCCTGCAGC | GTGCCTCTCC | AGCCACCTGC | CAACCGTAGA | GCTGCCCATC 2700 |
| CTCCTCTGGT | GGGAGTGGCC | TGCATGGTGC | CAGGCTGAGG | CCTAGTGTCA | GACAGGGAGC 2760 |
| CTGGAATCAT | AGGGATCCAG | GACTCAAAAG | TGCTAGAGAA | TGGCCATATG | TCACCATCCA 2820 |
| TGAAATCTCA | AGGGCTTCTG | GGTGGAGGGC | ACAGGGACCT | GAACTTATGG | TTTCCCAAGT 2880 |
| CTATTGCTCT | CCCAAGTGAG | TCTCCCAGAT | ACGAGGCACT | GTGCCAGCAT | CAGCCTTATC 2940 |
| TCCACCACAT | CTTGTAAAAG | GACTACCCAG | GGCCCTGATG | AACACCATGG | TGTGTACAGG 3000 |
| AGTAGGGGGT | GGAGGCACGG | ACTCCTGTGA | GGTCACAGCC | AAGGGAGCAT | CATCATGGGT 3060 |
| GGGGAGGAGG | CAATGGACAG | GCTTGAGAAC | GGGGATGTGG | TTGTATTTGG | TTTTCTTTGG 3120 |
| TTAGATAAAG | TGCTGGGTAT | AGGATTGAGA | GTGGAGTATG | AAGACCAGTT | AGGATGGAGG 3180 |
| ATCAGATTGG | AGTTGGGTTA | GATAAAGTGC | TGGGTATAGG | ATTGAGAGTG | GAGTATGAAG 3240 |
| ACCAGTTAGG | ATGAGGATC | AGATTGGAGT | TGGGTTAGAG | ATGGGTAAA | ATTGTGCTCC 3300 |
| GGATGAGTTT | GGGATTGACA | CTGTGGAGGT | GGTTTGGGAT | GGCATGGCTT | TGGGATGGAA 3360 |
| ATAGATTTGT | TTTGATGTTG | GCTCAGACAT | CCTTGGGGAT | TGAACTGGGG | ATGAAGCTGG 3420 |
| GTTTGATTTT | GGAGGTAGAA | GACGTGGAAG | TAGCTGTCAG | ATTTGACAGT | GGCCATGAGT 3480 |

```
TTTGTTTGAT GGGGAATCAA ACAATGGGGG AAGACATAAG GGTTGGCTTG TTAGGTTAAG    3540
TTGCGTTGGG TTGATGGGGT CGGGGCTGTG TATAATGCAG TTGGATTGGT TTGTATTAAA    3600
TTGGGTTGGG TCAGGTTTTG GTTGAGGATG AGTTGAGGAT ATGCTTGGGG ACACCGGATC    3660
CATGAGGTTC TCACTGGAGT GGAGACAAAC TTCCTTTCCA GGATGAATCC AGGGAAGCCT    3720
TAATTCACGT GTAGGGGAGG TCAGGCCACT GGCTAAGTAT ATCCTTCCAC TCCAGCTCTA    3780
AGATGGTCTT AAATTGTGAT TATCTATATC CACTTCTGTC TCCCTCACTG TGCTTGGAGT    3840
TTACCTGATC ACTCAACTAG AAACAGGGGA AGATTTTATC AAATTCTTTT TTTTTTTTT    3900
TTTTTTTTGA GACAGAGTCT CACTCTGTTG CCCAGGCTGG AGTGCAGTGG CGCAGTCTCG    3960
GCTCACTGCA ACCTCTGCCT CCCAGGTTCA AGTGATTCTC CTGCCTCAGC CTCCTGAGTT    4020
GCTGGGATTA CAGGCATGCA GCACCATGCC CAGCTAATTT TTGTATTTTT AGTAGAGATG    4080
GGGTTTCACC AATGTTTGCC AGGCTGGCCT CGAACTCCTG ACCTGGTGAT CCACCTGCCT    4140
CAGCCTCCCA AAGTGCTGGG ATTACAGGCG TCAGCCACCG CGCCCAGCCA CTTTTGTCAA    4200
ATTCTTGAGA CACAGCTCGG GCTGGATCAA GTGAGCTACT CTGGTTTAT TGAACAGCTG    4260
AAATAACCAA CTTTTTGGAA ATTGATGAAA TCTTACGGAG TTAACAGTGG AGGTACCAGG    4320
GCTCTTAAGA GTTCCGATT CTCTTCTGAG ACTACAAATT GTGATTTTGC ATGCCACCTT    4380
AATCTTTTTT TTTTTTTTT TAAATCGAGG TTTCAGTCTC ATTCTATTTC CCAGGCTGGA    4440
GTTCAATAGC GTGATCACAG CTCACTGTAG CCTTGAACTC CTGGCCTTAA GAGATTCTCC    4500
TGCTTCGGTC TCCCAATAGC TAAGACTACA GTAGTCCACC ACCATATCCA GATAATTTTT    4560
AAATTTTTG GGGGCCGGG CACAGTGGCT CACGCCTGTA ATCCCAACAC CATGGGAGGC    4620
TGAGATGGGT GGATCACGAG GTCAGGAGTT TGAGACCAGC CTGACCAACA TGGTGAAACT    4680
CTGTCTCTAC TAAAAAAAAA AAAATAGAA AAATTAGCCG GGCGTGGTGG CACACGGCAC    4740
CTGTAATCCC AGCTACTGAG GAGGCTGAGG CAGGAGAATC ACTTGAACCC AGAAGGCAGA    4800
GGTTGCAATG AGCCGAGATT GCGCCACTGC ACTCCAGCCT GGGTGACAGA GTGAGACTCT    4860
GTCTCAAAAA AAAAAATTT TTTTTTTT TTTGTAGAGA TGGATCTTGC TTTGTTTCTC    4920
TGGTTGGCCT TGAACTCCTG GCTTCAAGTG ATCCTCCTAC CTTGGCCTCG GAAAGTGTTG    4980
GGATTACAGG CGTGAGCCAC CATGACTGAC CTGTCGTTAA TCTTGAGGTA CATAAACCTG    5040
GCTCCTAAAG GCTAAAGGCT AAATATTTGT TGGAGAAGGG GCATTGGATT TTGCATGAGG    5100
ATGATTCTGA CCTGGGAGGG CAGGTCAGCA GGCATCTCTG TTGCACAGAT AGAGTGTACA    5160
GGTCTGGAGA ACAAGGAGTG GGGGGTTATT GGAATTCCAC ATTGTTTGCT GCACGTTGGA    5220
TTTTGAAATG CTAGGGAACT TTGGGAGACT CATATTTCTG GGCTAGAGGA TCTGTGGACC    5280
ACAAGATCTT TTTATGATGA CAGTAGCAAT GTATCTGTGG AGCTGGATTC TGGGTTGGGA    5340
GTGCAAGGAA AAGAATGTAC TAAATGCCAA GACATCTATT TCAGGAGCAT GAGGAATAAA    5400
AGTTCTAGTT TCTGGTCTCA GAGTGGTGCA GGGATCAGGG AGTCTCACAA TCTCCTGAGT    5460
GCTGGTGTCT TAGGGCACAC TGGGTCTTGG AGTGCAAAGG ATCTAGGCAC GTGAGGCTTT    5520
GTATGAAGAA TCGGGGATCG TACCCACCCC CTGTTTCTGT TTCATCCTGG GCATGTCTCC    5580
TCTGCCTTTG TCCCCTAGAT GAAGTCTCCA TGAGCTACAA GGGCCTGGTG CATCCAGGGT    5640
GATCTAGTAA TTGCAGAACA GCAAGTGCTA GCTCTCCCTC CCCTTCCACA GCTCTGGGTG    5700
TGGGAGGGGG TTGTCCAGCC TCCAGCAGCA TGGGGAGGGC CTTGGTCAGC CTCTGGGTGC    5760
CAGCAGGGCA GGGGCGGAGT CCTGGGGAAT GAAGGTTTTA TAGGGCTCCT GGGGGAGGCT    5820
CCCCAGCCCC AAGCTT                                                    5836
```

( 2 ) INFORMATION FOR SEQ ID NO:2:

( i ) SEQUENCE CHARACTERISTICS:
        ( A ) LENGTH: 1192 base pairs
        ( B ) TYPE: nucleic acid
        ( C ) STRANDEDNESS: single
        ( D ) TOPOLOGY: linear ( i i ) MOLECULE TYPE: DNA (genomic)

( x i ) SEQUENCE DESCRIPTION: SEQ ID NO:2:

```
TCTAGAAATC TAGCTGATAT AGTGTGGCTC AAAACCTTCA GCACAAATCA CACCGTTAGA      60
CTATCTGGTG TGGCCCAAAC CTTCAGGTGA ACAAGGGAC  TCTAATCTGG CAGGATATTC     120
CAAAGCATTA GAGATGACCT CTTGCAAAGA AAAAGAAATG GAAAAGAAAA AGAAAGAAAG     180
GAAAAAAAAA AAAAAAAAGA GATGACCTCT CAGGCTCTGA GGGGAAACGC CTGAGGTCTT     240
TGAGCAAGGT CAGTCCTCTG TTGCACAGTC TCCCTCACAG GGTCATTGTG ACGATCAAAT     300
GTGGTCACGT GTATGAGGCA CCAGCACATG CCTGGCTCTG GGGAGTGCCG TGTAAGTGTA     360
TGCTTGCACT GCTGAATGCT TGGGATGTGT CAGGGATTAT CTTCAGCACT TACAGATGCT     420
CATCTCATCC TCACAGCATC ACTATGGGAT GGGTATTACT GGCCTCATTT GATGGAGAAA     480
GTGGCTGTGG CTCAGAAAGG GGGGACCACT AGACCAGGGA CACTCTGGAT GCTGGGGACT     540
CCAGAGACCA TGACCACTCA CCAACTGCAG AGAAATTAAT TGTGGCCTGA TGTCCCTGTC     600
CTGGAGAGGG TGGAGGTGGA CCTTCACTAA CCTCCTACCT TGACCCTCTC TTTTAGGGCT     660
CTTTCTGACC TCCACCATGG TACTAGGACC CCATTGTATT CTGTACCCTC TTGACTCTAT     720
GACCCCCACT GCCCACTGCA TCCAGCTGGG TCCCTCCTA  TCTCTATTCC CAGCTGGCCA     780
GTGCAGTCTC AGTGCCCACC TGTTTGTCAG TAACTCTGAA GGGGCTGACA TTTTACTGAC     840
TTGCAAACAA ATAAGCTAAC TTTCCAGAGT TTTGTGAATG CTGGCAGAGT CCATGAGACT     900
CCTGAGTCAG AGGCAAAGGC TTTTACTGCT CACAGCTTAG CAGACAGCAT GAGGTTCATG     960
TTCACATTAG TACACCTTGC CCCCCCCAAA TCTTGTAGGG TGACCAGAGC AGTCTAGGTG    1020
GATGCTGTGC AGAAGGGGTT TGTGCCACTG GTGAGAAACC TGAGATTAGG AATCCTCAAT    1080
CTTATACTGG GACAACTTGC AAACCTGCTC AGCCTTTGTC TCTGATGAAG ATATTATCTT    1140
CATGATCTTG GATTGAAAAC AGACCTACTC TGGAGGAACA TATTGTATCG AT            1192
```